(12) United States Patent
Burnam

(10) Patent No.: US 10,966,927 B2
(45) Date of Patent: *Apr. 6, 2021

(54) PETROLATUM-BASED DELIVERY SYSTEMS AND FOR ACTIVE INGREDIENTS

(71) Applicant: GLOBAL HEALTH SOLUTIONS LLC, Rome, GA (US)

(72) Inventor: Bradley Burnam, Calabasas, CA (US)

(73) Assignee: GLOBAL HEALTH SOLUTIONS LLC, Rome, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/917,846

(22) Filed: Jun. 30, 2020

(65) Prior Publication Data

US 2020/0330381 A1    Oct. 22, 2020

Related U.S. Application Data

(63) Continuation of application No. 15/167,099, filed on May 27, 2016, now Pat. No. 10,722,461.

(60) Provisional application No. 62/182,034, filed on Jun. 19, 2015, provisional application No. 62/319,449, filed on Apr. 7, 2016, provisional application No. 62/326,150, filed on Apr. 22, 2016, provisional application No. 62/338,995, filed on May 19, 2016.

(51) Int. Cl.
| | |
|---|---|
| *A61K 9/10* | (2006.01) |
| *A61K 47/06* | (2006.01) |
| *A61K 9/00* | (2006.01) |
| *A61K 9/06* | (2006.01) |
| *A61K 38/20* | (2006.01) |
| *A61K 8/31* | (2006.01) |
| *A61K 38/18* | (2006.01) |
| *A61Q 19/00* | (2006.01) |
| *A61K 8/04* | (2006.01) |
| *A61K 31/785* | (2006.01) |
| *A61K 45/06* | (2006.01) |
| *A61K 8/00* | (2006.01) |

(52) U.S. Cl.
CPC .................. *A61K 9/10* (2013.01); *A61K 8/00* (2013.01); *A61K 8/044* (2013.01); *A61K 8/31* (2013.01); *A61K 9/0014* (2013.01); *A61K 9/06* (2013.01); *A61K 31/785* (2013.01); *A61K 38/1825* (2013.01); *A61K 38/1841* (2013.01); *A61K 38/20* (2013.01); *A61K 45/06* (2013.01); *A61K 47/06* (2013.01); *A61Q 19/00* (2013.01); *A61K 2800/10* (2013.01)

(58) Field of Classification Search
None
See application file for complete search history.

(56) References Cited

U.S. PATENT DOCUMENTS 4,929,442 A * 5/1990 Powell .................... A61P 35/00
424/85.2

* cited by examiner

*Primary Examiner* — David J Blanchard
*Assistant Examiner* — Sarah J Chickos
(74) *Attorney, Agent, or Firm* — Polsinelli PC

(57) ABSTRACT

The present disclosure is broadly concerned with petrolatum-based compositions as a suspension matrix for the active ingredients. The disclosure is also concerned with processes for forming stable emulsions of active ingredients in petrolatum.

9 Claims, 2 Drawing Sheets

PETROLATUM-BASED DELIVERY SYSTEMS AND FOR ACTIVE INGREDIENTS

CROSS-REFERENCE TO RELATED APPLICATIONS

This application is a continuation of U.S. application Ser. No. 15/167,099, filed May 27, 2016, which claims priority to U.S. Provisional Application No. 62/182,034, filed Jun. 19, 2015, U.S. Provisional Application No. 62/319,449, filed Apr. 7, 2016, U.S. Provisional Application No. 62/326,150, filed Apr. 22, 2016, and U.S. Provisional Application No. 62/338,995, filed May 19, 2016. The contents of all aforementioned applications are incorporated by reference in their entirety, for all purposes, herein.

FIELD

The present disclosure is broadly concerned with petrolatum-based compositions as a suspension matrix for active ingredients. The disclosure is also concerned with processes for forming stable emulsions of active ingredients in petrolatum.

BACKGROUND

Petrolatum is a semi-solid mixture of long chain (greater than C=20) hydrocarbons. Petrolatum is a known skin protectant and has been widely used in cosmetic and dermatological applications. Although petrolatum is known to have advantageous protective properties when applied to the skin, its hydrophobic nature had previously made it a poor candidate for formulating active ingredients. It was previously thought that an emulsifier would be necessary to disperse active ingredients throughout petrolatum. It was also thought that the petrolatum was incapable of delivering active ingredients because the active ingredients would be trapped within the petrolatum and therefore would be unable to reach the desired delivery site.

The Applicant has discovered that active ingredients can be formulated in petrolatum. The petrolatum-based compositions described herein contain nanodroplets of active ingredients dispersed in petrolatum. The nanodroplets release the active ingredients to the application site continuously. Additionally, the petrolatum-based compositions described herein are gentle. They do not irritate the skin and are not cytotoxic to mammalian cells. The Applicant has further discovered processes leading to a stable delivery system for a variety of ingredients.

BRIEF DESCRIPTION OF THE FIGURES

The application file contains at least one photograph executed in color. Copies of this patent application publication with color photographs will be provided by the Office upon request and payment of the necessary fee.

DETAILED DESCRIPTION

The disclosure provides for petrolatum-based compositions of active ingredients, processes for making petrolatum-based compositions of active ingredients, and applications and uses of petrolatum-based compositions described herein. The active ingredients of the present disclosure are dispersed throughout the petrolatum as nanodroplets with the petrolatum. The petrolatum serves as a suspension matrix for the active ingredients. Importantly, petrolatum-based compositions of the present disclosure do not contain an emulsifier. As it was discovered by the inventors, generally emulsifiers were not necessary for dispersing the active ingredient nanodroplets in the petrolatum. Surprisingly, compositions in accordance with the present disclosure are shelf stable for extended periods of time even under non-ideal conditions. In addition, the compositions exhibit exceptional chemical stability of the active ingredients, and are capable of delivering an active ingredient over extended periods of time to the desired site.

I. Compositions

The disclosure provides for compositions that are petrolatum-based. A petrolatum-based composition is made up primarily of petrolatum. The characteristics of a petrolatum-based composition differ from a composition containing only a small amount of petrolatum. In some embodiments, the petrolatum-based composition is greater than about 80% petrolatum. In other embodiments, the petrolatum-based composition is greater than about 81% petrolatum, greater than about 82% petrolatum, greater than about 83% petrolatum, greater than about 84% petrolatum, greater than about 85% petrolatum, greater than about 86% petrolatum, greater than about 87% petrolatum, greater than about 88% petrolatum, greater than about 89% petrolatum, greater than about 90% petrolatum, greater than about 91% petrolatum, greater than about 92% petrolatum, greater than about 93% petrolatum, greater than about 94% petrolatum, greater than about 95% petrolatum, greater than about 96% petrolatum, greater than about 97% petrolatum, greater than about 98% petrolatum, or greater than about 99% petrolatum. The petrolatum is preferably medical grade petrolatum.

The composition also contains one or more active ingredients dispersed throughout the petrolatum. The total amount of active ingredient in the composition generally constitutes less than about 1% by weight of the total composition. In preferred embodiments, the active ingredient constitutes from about 0.1% to about 0.5% by weight, or more preferably, from about 0.1% to about 0.3% by weight to the total composition.

The remaining weight of the composition, typically from about 0.1% to about 6% by weight of the petrolatum-based composition, is water or another solvent. In a preferred embodiment, the composition contains about 5% water.

Figure 1:
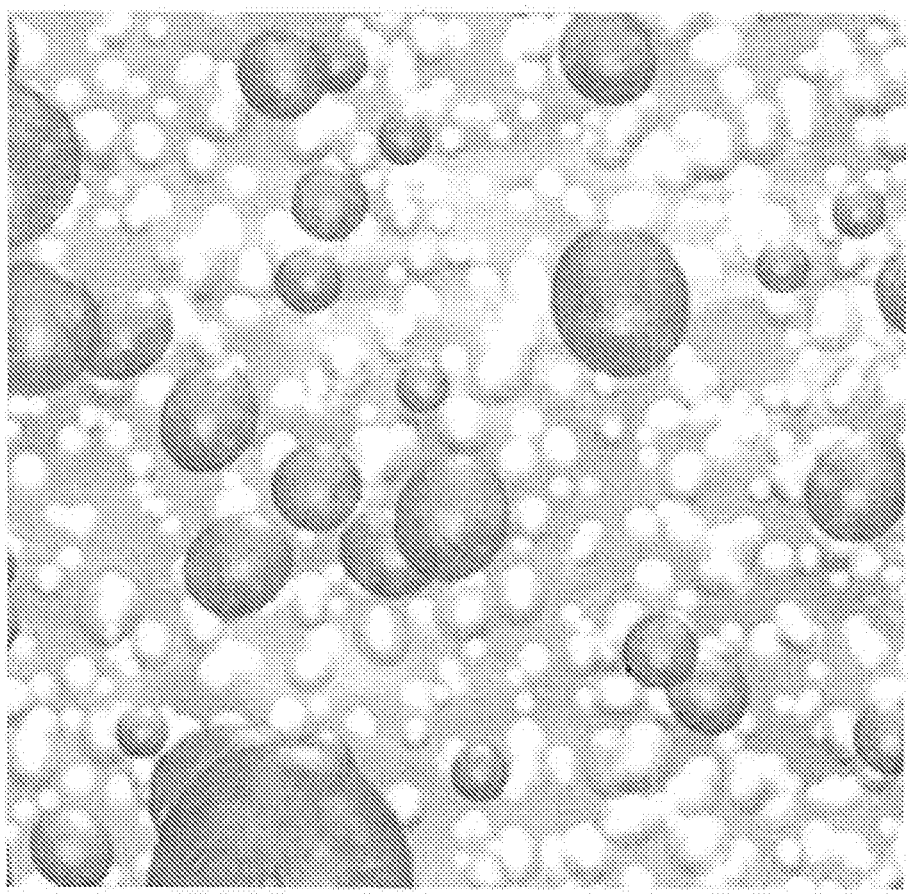
FIG. 1 depicts an image of the formulation structure when using the mixing methodology disclosed herein for permanently encapsulating active ingredients as nanodroplets into petrolatum.

Importantly, the active ingredients do not react with the petrolatum. Instead, the active ingredient is dispersed in the petrolatum as nanodroplets, and the petrolatum serves as a suspension matrix for the active ingredients. "Nanodroplet," as used herein, is an aggregation of molecules of active ingredient in the petrolatum base. The nanodroplets typically contain a small amount of solvent in addition to the active ingredient. Nanodroplets in accordance with the invention are shown in FIG. 1. The nanodroplets may vary in size but generally the longest dimension of the nanodroplets measures from about 10 nm to about 10,000 nm. In various embodiments, the nanodroplets range from about 10 nm to about 100 nm, from about 100 nm to about 1000 nm, from about 1000 nm to about 2000 nm, from about 2000 nm to about 3000 nm, from about 3000 nm to about 4000 nm, from about 4000 nm to about 5000 nm, from about 5000 nm to about 6000 nm, from about 6000 nm to about 7000 nm, from about 7000 nm to about 8000 nm, from about 8000 nm to about 9000 nm, from about 9000 nm to about 10,000 nm. The nanodroplets are dispersed through the petrolatum homogeneously.

In one embodiment, the compositions do not contain an emulsifier. An emulsifier, as used herein, is an added formulation ingredient used to reduce the tension between hydrophilic and hydrophobic surface ingredients, thereby facilitating the mixture hydrophilic and hydrophobic ingredients. In embodiments with an emulsifier, the HLB of the emulsifier is generally around 10.

The compositions described herein are stable. In one aspect, stability refers to the integrity of the composition as a whole, and in particular, the stability of the nanodroplets in the petrolatum. Under ambient conditions, the petrolatum and the active ingredients will not separate for greater than two years meaning that the composition is shelf stable for at least two years. Even under accelerated conditions, such as reduced pressure, the petrolatum and the active ingredients do not separate. In addition to the stability of the composition, the compositions also show exceptional chemical stability for the active ingredient. The chemical stability stems primarily from the low-temperature manufacturing process described below. The absence of excessive heat conditions in the manufacturing of the compositions improves the chemical stability (resistance to degradation) for the active ingredients.

In some embodiments, the petrolatum-based compositions described herein consist essentially of petrolatum, an active ingredient, and water. In other embodiments, the petrolatum-based compositions described herein consist of petrolatum, an active ingredient, and water.

The active ingredient may be a vitamin or supplement, a pharmaceutical, a biologic, or a cosmetic ingredient. The active ingredient may be a soluble ingredient. As used herein, a "soluble ingredient" refers to an ingredient (in its free base, free acid or salt form) having solubility in water or a polar solvent in excess of about 1 mg/ml at room temperature (20-25°). In certain embodiments, the soluble ingredient has a water solubility of about or greater than 5, 10, 20, 30, 40, 50, 60, 70, 80, 90, 100, 120, 140, 160, 180, 200, or 250 mg/mL at room temperature. The active ingredient may also be insoluble in water as described in more detail below.

In one embodiment, the active ingredient is a vitamin. Water-soluble vitamins include but are not limited to Vitamin C (ascorbic acid), Vitamin B1 (thiamine), Vitamin B2 (riboflavin), Vitamin B3 (niacin, nicotinic acid), Vitamin B5 (pantothenic acid), Vitamin B6 (pyridoxine), Vitamin B7 (biotin), Vitamin B9 (folic acid, folate, folacin), and Vitamin B12 (cobalamin). In another embodiment, the active ingredient is a supplement. The supplement may be chosen from pyruvate, creatine, Isoflavone, betaine HCl, psyllium, pantothenic Acid, zinc chloride, zinc gluconate, zinc sulfate, hytoestrogen, pycnogenol, proanthocyanidin, suntheanine, methylsulfonyl-methane, L-glutamine, colostrums, biotin, acetyl-L-carnitine, inositol, L-tyrosine, s-adenosyl methionine, bromelain, 2-dimethylaminoethanol, chromium picolinate, and combinations thereof. In another embodiment, the active ingredient is a pharmaceutical. Non-limiting examples of water soluble pharmaceuticals include verapamil HCl, potassium chloride, cefdnir, propafenone HCl, hydroxyurea, hydrocodone bitartrate, delavirdine mesylate, nelfinavir meslyate, pentosan polysulfate sodium, tocainide HCl, quetiapine fumarate, fexofenadine HCl, carafate, rifampin, moxifloxacin HCl, praziquantel, ciprofloxacin, phosphate sodium potassium, methenamine mandelate, sotalol HCl, cefprozil, cefadroxil, metformin HCl, irbesartan, nefazodone HCl, gatifloxacin, didanosine, modafinil, efavirenz, metaxalone, amantadine HCl, morphine sulfate, mefenamic acid, diltiazem HCl, sevelamer HCl, albendazole, amoxicilline, clavulanate potassium, lithium carbonate, lamivudine, sumatriptan succinate, nabumetone, zidovudine, cimetidine, chlorpromazine HCl, valacyclovir HCl, bupropion HCl, ranitidine, abacavir sulfate, acyclovir, aminobenzoate potassium, pyridostigmine bromide, potassium chloride, isosorbide mononitrate, nicin, demeclocycline HCl, cefixime, naproxen sodium, tetratcycline HCl, cefuroxime axetil, propoxyphene napsylate, pyrazinamide, flecainide acetate, simethicone, mebendazole, methdopa, chlorathiazide, indinavir, penicillamine, meyyrosine, losartan potassium, thiobendazole, norfloxacin, hydroxyurea, procainamide, entacapone, valsartan, terbinafine HCl, metaprolol tartrate, ofloxacin, levofloxacin, chlorzoxazone, tolmetin sodium, tramadol HCl, bepridil HCl, phenyloin sodium, atorvastatin calcium, gabapentine, celecoxib, fluconazole, doxepine HCl, trovafloxacin mesylate, azithromycin, sertraline HCl, rifabutin, cefpodoxime proxetil, mesalamine, etidronate disodium, nitrofurantoin, choline magnesium trisalicylate, theophylline, nizatidine, pancreatin, quinidine sulfate, methocarbamol, mycophenolate mefetil, ganciclovir, saquinavir mesylate, tolcapne, ticlopidine HCl, valganciclovir HCl, capecitabine, orlistat, colsevelam HCl, irbesartan, succimer, meperidine HCl, hydroxychloroquine sulfate, guaifenesin, eprosartan mesylate, aminodarone HCl, felbamate, pseudoephedrine sulfate, carisoprodol, venlafaxine, propanolol HCl, etodolac, acebutolol, and chondrotin. In yet another embodiment, the active ingredient is a biologic, such as collagen type 1, 2, and/or 3, and/or botanical ingredients used for biologic purposes such as to increase immunity to allergens. In still another embodiment, the active ingredient is a cosmetic ingredient. Non-limiting examples of cosmetic ingredients include 1,2-Hexanediol, 10-Hydroxydecanoic Acid, *Acacia farnesiana* extract, *Acacia senegal*, açai, Accutane, acerola fruit extract, acetic acid, acetone, acetyl carnitine HCL, acetyl glucosamine, acetyl glyceryl ricinoleate, acetyl hexapeptide-8, acetyl octapeptide-3, acetyl tributyl citrate, acetyl tyrosine, acetylated castor oil, acetylated hydrogenated cottonseed glyceride, acetylated lanolin, acetylated lanolin alcohol, acetylated palm kernel glycerides, acetylsalicylic acid, *Achillea millefolium*, acid, acne soap, acrylate, acrylates copolymer, acrylates/C10-30 alkyl acrylate crosspolymer, acrylates/dimethicone copolymer, acrylates/steareth-20 methacrylate copolymer, *Actaea racemosa*, active ingredient, adapalene, adenine, adenosine, adenosine triphosphate, adipic acid/neopentyl glycol/trimellitic anhydride copolymer, advanced glycation endproduct, *Aerocarpus santalinus, Aesculus hippocastanum*, agar, *Agaricus bisporus* extract, AGE, *Agrimonia eupatoria* leaf extract, AHA, *Ahnfeltia concinna* extract, *ahnfeltia* extract, *Ajuga turkestanica* extract, alanine, *Alaria esculenta*, albumin, *Alchemilla vulgaris*, alcloxa, alcohol, *Aleurites moluccana* seed oil, alfalfa extract, algae, algae extract, algin, aliphatic hydrocarbon, alkaline, alkyloamides, all-trans retinoic acid, allantoin, allyl methacrylates crosspolymer, almond oil, *Aloe barbadensis, aloe barbadensis* leaf juice extract, *aloe barbadensis* leaf juice powder, *aloe* extract, *aloe* juice, *aloe vera*, alpha bisabolol, alpha glucan oligosaccharide, alpha hydroxy acid, alpha isomethyl ionone, alpha lipoic acid, alpha-tocopherol, *Alteromonas ferment* extract, *Althaea rosea, Althea officinalis*, alumina, aluminum, aluminum chlorohydrate, Aluminum hydroxide, aluminum magnesium silicate, aluminum powder, aluminum silicate, aluminum starch octenylsuccinate, aluminum stearate, aluminum sulfate, amino acid, aminobutyric acid, aminomethyl propanediol, aminomethyl propanol, aminophylline, ammonium acryloyldimethyltaurate/VP copolymer, ammonium chloride, ammonium glycolate, ammonium hydroxide, ammonium laureth sulfate, ammonium lauryl sulfate, amniotic extract or fluid, amodimethicone, amygdalic acid, amyl cinnamate, amyl salicylate, amyris oil, *Anacyclus pyrethrum, Anacystis nidulans* extract, *Ananas sativus* fruit extract, andiroba oil, *Anethum graveolens, Angelica archangelica* root oil, *Angelica polymorpha sinensis* root extract, anisaldehyde, anise, annato extract, *Anthemis nobilis* flower extract, anthocyanin, anti-inflammatory, anti-irritant, antibacterial, antioxidant, apple fruit extract, apricot kernel, apricot kernel oil, aquaporins, arachidic acid, arachidonic acid, arachidyl alcohol, arachidyl glucoside, arachidyl propionate, *Arachis hypogaea* extract, arbutin, *Arctium lappa, Arctostaphylos uva ursi* leaf, argan oil, *Argania spinosa*, arginine, Argireline, arnica extract, aroma/flavor, arrowroot, artemia extract, *Artemisia absinthium* extract, *Artemisia vulgaris, Ascophyllum nodosum*, ascorbic acid, ascorbyl glucosamine, ascorbyl glucoside, ascorbyl methylsilanol pectinate, ascorbyl palmitate, asparagine, *Asparagopsis armata* extract, aspartic acid, astaxanthin, astaxanthin extract, *Astragalus membranaceus, Astragalus sinicus, Astrocaryum murumuru* seed butter, atelocollagen, ATP, *Atractyloydes lancea* root extract, *Avena sativa*, avobenzone, avocado oil, awapuhi, *Azadirachta indica*, azelaic acid, Azelex, azuki beans, azulene, babassu oil, *Bacillus subtilis*, bakuchiol, balm mint extract, balsam peru, *Bambusa vulgaris* (bamboo) leaf/stem extract, banana extract, barberry, barium sulfate, barley extract, batyl alcohol, bay leaf oil, bearberry extract, bee pollen, beet root extract, behenic acid, behentrimonium chloride, behenyl alcohol, *Bellis perennis*, bentonite, benzalkonium chloride, benzephenone-3, benzocaine, benzoic acid, benzoin extract, benzophenone, benzothonium chloride, benzoyl peroxide, benzyl alcohol, benzyl salicylate, *Berberis aristata*, bergamot oil, *Bertholletia excelsa* extract, beta hydroxy acid, *Beta vulgaris* root extract, beta-carotene, beta-glucan, beta-sitosterol, *Betula alba*, BHA (beta hydroxy acid), BHT, bifida ferment lysate, bifidus extract, bilberry extract, bimatoprost, bioflavonoid, biotin, birch bark extract, birch leaf extract, bis-diglyceryl polyacyladipate, bis-phenylpropyl dimethicone, bisabolol, bismuth oxychloride, bitter orange flower, black cohosh, black currant oil, black elderberry, black locust extract, black mulberry, black pepper extract and oil, black raspberry, black tea, blackberry, bladderwrack extract, bloodwort, blue 1, blue 1 lake, *Boerhavia diffusa* root extract, bois de rose oil, bois oil, borage seed extract, borage seed oil, *Borago officinalis* extract, *Borago officinalis* seed oil, borate, borax, boric acid, boron nitride, *Boswellia carterii, Boswellia serrata* extract, botanicals, boysenberry, *Brassica campestris*, Brazil nut extract, broad spectrum, bromelain, bronopol, bronze powder, *Buddleja davidii* extract, bumetrizole, *Bupleurum falcatum* extract, burdock root, butcher's broom extract, butyl acetate, butyl methoxydibenzoylmethane, butylene glycol, butylparaben, butylphenyl methylpropional, *Butyrospermum* fruit, *Butyrospermum parkii, Buxus chinensis*, C10-30 cholesterol/lanosterol esters, C12-15 alkyl benzoate, C12-18 acid triglyceride, C13-14 isoparaffin, C18-36 acid triglyceride, C20-40 pareth-40, caffeic acid, caffeine, cajeputi oil, calamine, calcium ascorbate, calcium carbonate, calcium d-pantetheines-sulfonate, calcium gluconate, calcium pantetheine sulfonate, calcium pantothenate, *calendula* extract, *Calendula officinalis* flower extract, *Calluna vulgaris* flower extract, *Calophyllum inophyllum* seed oil, *Camellia japonica, Camellia oleifera, Camellia sinensis*, camphor, cananga extract, *Cananga odorata*, candelilla wax, *Cannabis sativa* L. oil, canola oil, Caprooyl Tetrapeptide-3, caprylic/capric triglyceride, caprylyl glycol, caprylyl methicone, capsaicin, capsicum, capsicum oleoresin, caramel, carbomer, carbopol, carboxylic acid, cardamom, carmine, carnauba wax, carnitine, carnosic acid, carnosine, carnosol acid, carrageenan, carrot oil, *Carthamus tinctorius* oil, carvone, *Carya illinoensis* oil, casein, *Castanea sativa* seed extract, castor isostearate succinate, castor oil, catalase, *Caulerpa taxifolia* extract, cedarwood, *Cedrus atlantica* bark extract, celandine, cell-communicating ingredients, cellulose, Cellulose gum, *Centaurea cyanus, Centella asiatica*, cephalin, *Cera alba*, cera microcristallina, ceramide AP, ceramide EOP, ceramide NP, ceramide NS, ceramides, ceresin, ceteareth-20, cetearyl alcohol, cetearyl ethylhexanoate, cetearyl glucoside, cetearyl octanoate, cetyl acetate, cetyl alcohol, cetyl dimethicone, cetyl dimethicone copolyol, cetyl esters, cetyl hydroxyethylcellulose, cetyl palmitate, cetyl PEG/PPG-10/1-dimethicone, chamomile, *Chamomilla recutita* flower extract, chaparral extract, charcoal, chaulmoogra oil, chelating agent, cherry extract, China clay, chitosan, chlorella, chlorhexidine, chlorophene, chloroxylenol, chlorphenesin, cholecalciferol, cholesterol, choline, chondroitin sulfate, *Chondrus crispus*, chromium hydroxide green, chromium oxide green, *chrysanthemum* extract, *Chrysanthemum parthenium* extract, *Cichorium intybus, Cimicifuga racemosa* root extract, *Cinnamomum, Cinnamomum camphora*, cinnamon, cinnamyl alcohol, citric acid, citronellol, *Citrullus colocynthis, Citrus amara, Citrus aurantifolia, Citrus aurantium, Citrus aurantium* extract, *Citrus medica limonium, Citrus unshiu, Citrus unshiu* peel extract, clary oil, clay, clove leaf, clove oil, clover blossom, clover leaf oil, cocamide DEA and MEA, cocamidopropyl betaine, cocamidopropyl dimethylamine, cocamidopropyl hydroxysultaine, coco-glucoside, cocoa butter, cocoa extract, cocoglycerides, coconut, coconut oil, *Cocus nucifera, Codium tomentosum* extract, coenzyme Q10, *Coffea arabica* (coffee) seed oil, *Coffea arabica* extract, *Cola acuminata* seed extract, *Coleus barbatus*, collagen, collagen amino acid, colloidal oatmeal, colloidal silver, colostrum, coltsfoot, comfrey extract, *Commiphora myrrha* extract, coneflower, *Copaifera officinalis, Copernicia cerifera* wax, copper gluconate, copper lysinate/prolinate, copper PCA, copper peptides, copper sulfate, *Corallina officinalis* extract, coriander, corn oil, cornflower, cornmint, cornstarch, *Cornus* extract, *Corylus americana, Corylus avellana*, coumarin, counter-irritant, cranberry seed extract, cranberry seed oil, *Crataegus monogina* extract, creatine, creatinine, cucumber extract, *Cucumis melo* (melon) fruit extract, *Cucumis sativus* extract, *Cucurbita pepo* seed extract, *Cucurbitea peponis, Curcuma longa* root, curcumin, *Cyamopsis tetragonoloba*, cyanocobalamin, cyclamen aldehyde, cyclohexasiloxane, cyclomethicone, cyclopentasiloxane, cyclotetrasiloxane, Cymbopogon citrates, *Cymbopogon martini*, cysteine, cystine, cytochrome, cytokines, D&C, D&C colors, d-alpha-tocopherol, daisy flower extract, dandelion extract, *Daucus carota*, DEA, DEA oleth-10 phosphate, Dead Sea minerals, decarboxy carnosine HCL, decyl glucoside, decyl oleate, decylene glycol, dehydroacetic acid, dehydroepiandrosterone, deionized/demineralized water, denatured alcohol, deoxyribonucleic acid, detergent cleansing agent, deuterium oxide, dextran, dextrin, DHA, DHEA, di-PPG-3 myristyl ether adipate, diatomaceous earth, diazolidinyl urea, dibutyl phthalate, dicaprylyl carbonate, dicetyl phosphate, diethanolamine, diethylhexyl carbonate, diethylhexyl malate, diethylhexyl syringylidenemalonate, Differin, dihydrocholeth-30, dihydroxyacetone, diisopropyl adipate, diisopropyl dimer dilinoleate, diisostearoyl trimethylolpropane siloxy silicate, diisostearyl dimer dilinoleate, diisostearyl malate, dill extract, dimer dilinoleyl dimer dilinoleate, dimethicone, dimethicone copolyol, dimethicone crosspolymer, dimethicone/PEG-10/15 crosspolymer, dimethicone/vinyl dimethicone crosspolymer, dimethiconol, dimethyl capramide, dimethyl ether, dimethyl isosorbide, dimethyl MEA, dimethylaminoethanol (DMAE), *Dioscorea villosa* extract, dipentaerythrityl hexacaprylate/hexacaprate, dipotassium glycyrrhizate, dipotassium glycyrrhizinate, dipropylene glycol, disodium cocoamphodiacetate, disodium cocoyl glutamate, disodium diglyceryl phosphate, disodium EDTA, disodium glyceryl phosphate, disodium lauraminopropionate, disodium lauriminodipropionate tocopheryl phosphates, disodium rutinyl disulfate, disteardimonium hectorite, DMAE, DMDM hydantoin, DNA, docosahexaenoic acid, dog rose, dogwood, dong quai, Dromiceius oil, dulse, durian, *Durvillaea antarctica* extract, ecamsule, *Echium plantagineum* seed oil, ectoin, EDTA, egg yolk, eicosapentaenoic acid, *Elaeis guineensis*, elastin, elderberry, elecampane, ellagic acid, emollient, emu oil, emulsifier, English ivy extract, ensulizole, *Enteromorpha compressa* extract, enzymes, epidermal growth factor (EGF), epigallocatechin gallate, *Epilobium angustifolium* extract, *Equisetum arvense*, ergocalciferol, ergothioneine, *Eriobotrya japonica*, erythropoietin (Epo), erythrulose, escin, esculin, essential oil, ester, Ester-C, estradiol, ethanol, ethoxydiglycol, ethyl alcohol, ethyl macadamiate, ethyl vanillin, ethylhexyl methoxycinnamate, ethylhexyl palmitate, ethylhexyl stearate, ethylhexylglycerin, ethylparaben, eucalyptus extract, eucalyptus oil, *Eugenia aromatica, Eugenia caryophyllus*, eugenol, *Euphorbia cerifera* wax, *Euphrasia officinalis, Euterpe oleraca*, evening primrose oil, *Evodia rutaecarpa* extract, Ext. D&C, eyebright, faex, *Fagus sylvatica* extract, farnesol, farnesyl acetate, fatty acid, fatty alcohol, FD&C, FD&C colors, fennel oil, fennel seed extract, ferric ammonium ferrocyanide, ferric ferrocyanide, *Ferula foetida, Ferula galbaniflua*, ferulic acid, feverfew extract, fibroblast growth factor (FGF), fibronectin, *Ficus carica* fruit extract, fig, *Filipendula glaberrima, Filipendula rubra*, film-forming agent, fir needle oil, fireweed extract, fish cartilage extract, flavonoid, flavor, flax, flaxseed oil, floralozone, *Foeniculum vulgare* extract, folic acid, formaldehyde-releasing preservative, fragrance, frankincense extract, free-radical damage, fructose, fruit acid, Fu ling, *Fucus vesiculosus* extract, fuller's earth, fumaric acid, GABA, galactoarabinan, galbanum, gamma linolenic acid (GLA), *Ganoderma lucidum* extract, *Gardenia florida* extract, gelatin, *Gellidiela acerosa* extract, genistein, *Gentiana lutea* (Gentian) root extract, geraniol, geranium extract, geranium oil, Geranium pretense, Germaben II, ginger extract, ginger oil, *Ginkgo biloba* leaf extract, ginseng, GLA, glabridin, gluconolactone, glucosamine HCL, glucose, glucose oxidase, glucose tyrosinate, glucosyl hesperidin, glutamic acid, glutamine, glutathione, gluten ingredients, glycereth-26, glycereth-26 phosphate, glycereth-6 laurate, glycerin, glycerine, glycerol, glycerol monostearate, glycerol triacetate, glycerol trioleate, glyceryl behanate, glyceryl cocoate, glyceryl dibehanate, glyceryl dipalmitate, glyceryl distearate, glyceryl ester, glyceryl isopalmitate, glyceryl isostearate, glyceryl myristate, glyceryl oleate, glyceryl palmitate, glyceryl polymethacrylate, glyceryl stearate, glyceryl stearate SE, glycine, *Glycine soja* oil, *Glycine soja* seed extract, *Glycine soja* sterols, glycogen, glycol stearate, glycolic acid, glycolipid, glycoproteins, glycosaminoglycans, glycosphingolipid, glycyrrhetic acid, *Glycyrrhiza glabra, Glycyrrhiza uralensis* root extract, goji fruit extract, gold, goldenseal, *Gossypium herbacuem* seed oil, gotu kola, grape seed extract, grape seed oil, grapefruit oil, grapefruit peel extract, grapefruit seed extract, green tea, gromwell, guaiac wood, *Guaiacum officinale*, guar gum, guar hydroxypropyltrimonium chloride, guarana, gums, *Haematococcus pluvialis* extract, *Hamamelis virginiana*, hamamelitannin, *Haslea ostrearia* extract, hawthorn extract, hayflower extract, hazelnut oil, heavy water, *Hedera* helix, hedione, *Helianthus annuus* seed oil, *Helianthus* oil, hemp seed oil, hepatocyte growth factor (HGF), hesperidin, hesperidin methyl chalcone, hexyl cinnamal, hexyl laurate, hexyldecanol, hexylene glycol, hexylresorcinol, hibiscus, *Himanthalia elongate* extract, *Hippophae rhamnoides*, histidine, hoelen, homosalate, honey, honey extract, honeysuckle flower extract, hops, *Hordeum vulgare* extract, horse chestnut extract, horse elder, horseradish, horsetail extract, *Hortonia floribunda* leaf extract, Huang qi, human growth factor, humectant, *Humulus lupulus* extract, hyaluronic acid, *Hydnocarpus anthelmintica, Hydrastis canadenis*, hydrocortisone, hydrocotyl extract, hydrogen peroxide, hydrogenated coco-glyceride, hydrogenated didecene, hydrogenated lecithin, hydrogenated olive oil, hydrogenated palm glycerides, hydrogenated polydecene, hydrogenated polyisobutene, hydrogenated soybean oil, hydrogenated vegetable glycerides citrate, hydrolyzed collagen, hydrolyzed corn starch, hydrolyzed glycosaminoglycans, hydrolyzed jojoba esters, hydrolyzed jojoba protein, hydrolyzed silk, hydrolyzed vegetable protein, hydrolyzed wheat protein, hydroquinone, hydroxyethyl acrylate/sodium acryloyldimethyl taurate copolymer, hydroxyethylcellulose, hydroxylated lecithin, hydroxyproline, hydroxypropyl guar, hydroxypropyl starch phosphate, Hypericum extract, hypoallergenic, hyssop, idebenone, *Ilex paraguariensis, Illicium vernum*, imidazolidinyl urea, inactive ingredient, inositol, insulinlike growth factor (IGF), intercellular matrix, interleukin (IL), *Inula helenium*, iodopropynyl butylcarbamate, *Iris florentina* extract, Irish moss extract, iron oxides, iron powder, beeswax, isobutyl acetate, isobutylparaben, isocetyl salicylate, isododecane, isoflavone, isohexadecane, isoleucine, isononyl isononanoate, isoparaffin, isopropyl alcohol, isopropyl cloprostenate, isopropyl isostearate, isopropyl lanolate, isopropyl myristate, isopropyl palmitate, isopropyl titanium triisostearte/triethoxycaprylylsilane crosspolymer, isostearamide DEA, isostearic acid, isotretinoin, ivy extract, Japan wax, jasmine oil, *Jasminium grandiflorum*, jewelweed, jojoba butter, jojoba esters, jojoba oil, jojoba wax, jonquil extract, Ju hua, jujube fruit extract, juniper berry, *Juniperus communis*, kaolin, Kathon CG, kava-kava extract, kawa extract, kelp extract, *Kigelia africana* extract, kinetin, kiwi fruit extract, kojic acid, kojic dipalmitate, kola nut, kudzu root, kukui nut oil, L-ascorbic acid, L-carnitine, L-cysteine, lactic acid, *Lactobacillus bifidus*, lactobionate, lactobionic acid, lactoperoxidase, lady's mantle extract, lady's thistle (milk thistle) extract, *Lagerstroemia indica* extract, *Laminaria digitata, Laminaria longicruris, Laminaria ochroleuca* extract, *Laminaria saccharine, Lamium*

*album* flower extract, lanolin, lanolin alcohol, lappa extract, *Larrea divaricata* extract, *Larrea tridentata*, Latisse, lauramphocarboxyglycinate, laurdimonium hydroxypropyl hydrolyzed soy protein, laurdimonium hydroxypropyl hydrolyzed wheat protein, laureth-23, laureth-4, laureth-7, laureths, lauric acid, lauroyl lysine, *Laurus nobilis*, lauryl alcohol, lauryl glucoside, lauryl lactate, lauryl PEG-9 polydimethylsiloxyethyl dimethicone, lavandin oil, *Lavandula angustifolia*, *Lavandula officinalis*, lavender extract and oil, lecithin, lemon, lemon balm, lemon juice, lemon oil, lemongrass extract, lemongrass oil, lentil fruit extract, *Lentinus edodes* extract, *Leontopodium alpinum* extract, *Leptospermum scoparium* oil, leucine, *Levisticum officinale* root extract, licorice extract, licorice root, *Lilium candidum* bulb extract, lime oil and extract, *Limnanthes alba*, *Limnanthes alba* seed oil, limonene, linalool, linden flower extract, linoleic acid, linolenic acid, linseed oil, *Linum usitatissimum* extract, lipid, liposomes, lithium magnesium sodium silicate, *Lithospermum erythrorhizon*, *Litsea cubeba*, locust bean, *Lonicera caprifolium* flower extract, *Lonicera japonica*, *Lonicera japonica* flower extract, loquat extract, lotus seed extract, lovage root extract, *Luffa cylindrica* seed oil or extract, lupine, lupine oil, *Lupinus albus* extract, lutein, *Lycium barbarum* fruit extract, lycopene, lye, lysine, macadamia nut oil, Mad cow disease, madecassoside, magnesium, magnesium aluminum silicate, magnesium ascorbyl palmitate, magnesium ascorbyl phosphate, magnesium carbonate, magnesium gluconate, magnesium hydroxide, magnesium laureth sulfate, magnesium oleth sulfate, magnesium stearate, magnesium sulfate, malic acid, mallow, *Malva sylvestris* extract, malvaceae extract, mandarin orange oil or extract, mandelic acid, manganese gluconate, manganese violet, *Mangifera indica* (mango) seed butter, *Mangifera indica* root, manuka oil, marigold, marionberry, marjoram, marshmallow, *Mastocarpus stellatus*, mate extract, matricaria flower extract, matricaria oil, matrix metalloproteinases, MEA, meadowfoam seed oil, meadowsweet extract, *Medicago sativa*, *Melaleuca alternifolia*, *Melaleuca cajeputi* oil, *Melia azadirachta*, melibiose, *Melissa officinalis*, *Mentha arvensis*, *Mentha piperita*, *Mentha spicata*, *Mentha viridis*, menthol, menthone, menthoxypropanediol, menthyl anthranilate, menthyl lactate, meradmiate, methanol, methicone, methionine, methyl gluceth-20, methyl glucose sesquistearate, methyl trimethicone, methylchloroisothiazolinone, methyldibromo glutaronitrile, methyldihydrojasmonate, methyleugenol, methylglucoside phosphate, methylisothiazolinone, methylparaben, methylpropanediol, methylsilanol mannuronate, methylsilanol PEG-7 glyceryl cocoate, methylsufonylsulfate, methylsulfonylmethane, Mexoryl SX, mica, microcrystalline wax, *Microcystis aeruginosa*, milk protein, milk vetch root, millet seed extract, mimosa oil or extract, mineral oil, mint, *Mitracarpe scaber* extract, mixed fruit extracts, montan wax, montmorillonite, *Morinda citrifolia*, *Morus bombycis* root extract, *Morus nigra* root extract, mucopolysaccharide, *Mucor miehei* extract, mugwort extract, mulberry extract, murumuru seed butter, myristic acid, myristyl myristate, myristyl nicotinate, myrrh, myrtle extract, *Myrtus communis* extract, N-acetyl-L tyrosine, N6-furfuryladenine, nanoparticles, nanotechnology, NaPCA, *Narcissus poeticus* wax, *Nardostachys jatamansi*, *Nasturtium officinale* extract, natto gum, natural ingredient, natural moisturizing factor (NMF), neem extract or oil, neopentyl glycol dicaprylate/dicaprate, neopentyl glycol diheptanoate, neroli, neroli oil, nettle extract, niacin, niacinamide, nicotinamide, nicotinic acid, nitrogen, noni juice, nonoxynols, nordihydroguaiaretic acid, nylon-12, *Nymphaea tetragona*, o-cymen-5-ol, oak root extract, oat beta-glucan, oat bran extract, oat kernel extract, oatmeal, octinoxate, octisalate, octocrylene, octyl methoxycinnamate, octyl palmitate, octyl salicylate, octyl stearate, octyldodecanol, octyldodecyl myristate, octyldodecyl neopentanoate, *Oenothera biennis* oil, *Olea europaea* fruit oil, *Olea europaea* oil unsaponifiables, oleanolic acid, oleic acid, oleth-10, oleths, oleyl erucate, olibanum extract, olive oil/olive fruit oil, opium poppy seed, orange blossom, *Orbignya martiana*, *Orbignya oleifera*, orchid, oregano, *Origanum majorana*, *Origanum vulgare* flower extract, orris root, Ortho Tri-Cyclen, *Oryza sativa* cera, *Oryza sativa* oil, oryzanol, oxidoreductase, oxybenzone, oxygen, ozokerite, *P. elisabethae*, PABA, padimate O, *Padina pavonica* extract, *Paeonia albiflora* extract, *Paeonia suffruticosa* extract, palm kernel acid, palm oil, *Palmaria palmata* extract, palmarosa oil, palmitic acid, palmitoyl hexapeptide-12, palmitoyl oligopeptide, palmitoyl pentapeptide-3, palmitoyl tetrapeptide-7, palmitoyl tripeptide-1, Palmitoyl Tripeptide-38, palmitoyl tripeptide-5, *Panax ginseng* root extract, *Panicum miliaceum*, pansy extract, pantethine, panthenol, pantothenic acid, papain, *Papaver somniferum* seed, papaya extract, para-aminobenzoic acid (PABA), parabens, paraffin, *Paraffinum liquidum*, Parsol 1789, *Passiflora edulis* extract, *Passiflora edulis* seed oil, passion fruit extract, patchouli, *Paullinia cupana* seed extract, pawpaw extract, peanut oil, pecan oil, pectin, PEG 90M, PEG compound, PEG-10 dimethicone, PEG-10 dimethicone/vinyl dimethicone crosspolymer, PEG-10 rapeseed sterol, PEG-100 stearate, PEG-12 dimethicone, PEG-120 methyl glucose dioleate, PEG-14, PEG-150 distearate, PEG-20 methyl glucose sesquistearate, PEG-32, PEG-33, PEG-40 hydrogenated castor oil, PEG-40 stearate, PEG-60 almond glycerides, PEG-60 hydrogenated castor oil, PEG-7 glyceryl cocoate, PEG-75 shea butter glycerides, PEG-8, PEG-8 dimethicone, PEG-80 sorbitan laurate, PEG/PPG-17/6 copolymer, PEG/PPG-18/18 dimethicone, PEG/PPG-18/4 copolymer, PEG/PPG-20/15 dimethicone, PEG, *Pelargonium graveolens* oil, pellitory, pentadecalactone, pentaerythrityl tetraisostearate, pentaerythrityl tetraoctanoate, pentapeptides, pentasodium pentetate, pentylene glycol, peony flower, peony root extract, peppermint, peptides, perfluorocarbons, *Perilla ocymoides*, *Persea gratissima* oil, *Persicaria hydropiper*, petitgrain mandarin, petrolatum, PHA, phenoxyethanol, phenoxyisopropanol, phenyl trimethicone, phenylalanine, phenylethyl resorcinol, phloretin, phosphatidylcholine, phosphatidylethanolamine, phospholipid, phosphoric acid, photosensitizer, phthalates, *Phyllanthus emblica* fruit extract, phytantriol, phytic acid, phytoestrogen, phytonadione, phytosphingosine, phytosterol, *Picea abies* extract, pine oil, pineapple extract, pinecone extract, *Pinus lambertiana* wood extract, *Pinus sylvestris* extract, *Piper nigrum*, pistachio seed oil, *Pistacia vera* seed oil, *Pisum sativum*, plankton extract, plasticizing agents, *Plectranthus barbatus* extract, plum extract, plum seed oil, *Pogostemon cablin*, poloxamer 184, Poloxamer 407, poloxamers, polyacrylamide, polyacrylate-17, polyaminopropyl biguanide, polybutene, polycaprolactone, polyethylene, polyethylene glycol, polyglucuronic acid, polyglycerol monostearate, polyglyceryl 2 triisostearate, polyglyceryl methacrylate, polyglyceryl-3 beeswax, polyglyceryl-3 methylglucose distearate, polyglyceryl-4 isostearate, polyglyceryl-6 isostearate, *Polygonum cuspidatum* root extract, polyhydroxy acid, polyhydroxystearic acid, polyisobutene, polymer, polymethyl methacrylate, polymethylsilsesquioxane, polypropylene glycol, polyquaternium-10, polyquaterniums, polysaccharide, polysilicone-11, polysorbate 20, polysorbate 60, polysorbate 80, polysorbates, polyvinyl alcohol, polyvinylpyrrolidone, pomegranate extract, *Poria cocos* extract, *Porphyridium cruentum* extract, *Portulaca oleracea* extract, potassium, potassium ascorbyl tocopheryl phosphate, potassium cetyl phosphate, potassium hydroxide, potassium myristate, potassium phosphate, potassium sorbate, PPG-12 buteth-16, PPG-12/SMDI copolymer, PPG-14 butyl ether, PPG-2 myristyl ether propionate, PPG-2-deceth-30, PPG-20 methyl glucose ether, PPG-26-Buteth-26, PPG-3 benzyl ether myristate, pregnenolone acetate, preservatives, progesterone USP, proline, propanediol, propolis, propylene carbonate, propylene glycol, propylene glycol dicaprylate/dicaprate, propylene glycol isostearate, propylene glycol laurate, propylene glycol stearate, propylparaben, prostaglandin analogue, proteases, protein, *Prunella vulgaris, Prunus americana, Prunus amygdalus dulcis, Prunus armeniaca, Prunus domestica* seed extract, *Prunus domestica* seed oil, *Prunus dulcis, Pseudopterogorgia elisabethae, Pueraria lobata*, pullulan, pumpkin, pumpkin seed extract, *Punica granatum* extract, purified water, PVM/MA decadiene crosspolymer, PVP, PVP copolymer, PVP/dimethylaminoethylmethacrylate, pycnogenol, pyridoxine hydrochloride (HCL), *Pyrus cydonia, Pyrus malus*, quaternium ammonium compounds, quaternium-15, quaternium-18 hectorite, quercetin, *quercus, Quercus infectoria* extract, quillaja extract, quince seed, quinoa oil, *Ranunculus ficaria* extract, rapeseed oil, raspberry seed extract, raspberry seed oil, red 27 lake, red 33, red 6 lake, red algae, red clover, red raspberry extract, red sandalwood, reducing agent, Renova, resorcinol, resveratrol, Retin-A, retinoids, retinol, retinyl ascorbate, retinyl palmitate, retinyl retinoate, riboflavin, rice bran oil, rice oil, rice starch, ricinoleate, *Ricinus communis*, RNA, *Robinia pseudacacia* extract, *Rosa canina, Rosa centifolia, Rosa centifolia* flower, *Rosa damascena* oil, *Rosa eglanteria, Rosa gallica* flower extract, *Rosa mosqueta, Rosa roxburghii* extract, *Rosa rubiginosa*, rose flower, rose flower oil, rose hip, rose hip oil, rose oil, rosemary extract, rosemary oil, rosewood oil, *Rosmarinus officinalis* extract, royal jelly, *Rubus idaeus, Rubus occidentalis, Rubus ursinus, Rubus ursinus* x *idaeus, Rubus villoscus*, ruscogenine, *Ruscus aculeatus*, rutin, saccharide isomerate, saccharides, *Saccharomyces* calcium ferment, *Saccharomyces cerevisiae, Saccharomyces* copper ferment, *Saccharomyces* iron ferment, *Saccharomyces* lysate, *Saccharomyces* magnesium ferment, *Saccharomyces* manganese ferment, *Saccharomyces officinarum* ferment, *Saccharomyces* potassium ferment, *saccharomyces* selenium ferment, *Saccharomyces* silicon ferment, *Saccharomyces* zinc ferment, safflower seed oil, sage extract, salicin, salicylic acid, *Salix alba* extract, *Salix nigra* (willow) bark extract, *Salvia officinalis, Sambucus canadensis, Sambucus cerulea, Sambucus nigra*, sandalwood oil, *Santalum album* seed extract, *Sapindus mukurossi* peel extract, *Saponaria officinalis* extract, saponin, *Sargassum filipendula* extract, sausurrea oil, saw palmetto extract, *Saxifraga sarmentosa* extract, sclareolide, *Sclerocarya birrea*, sclerotium gum, *Scutellaria baicalensis* extract, SD alcohol, SD alcohol 40-2, sea buckthorn, sea salt, sea whip extract, Seamollient, seaweed, sebacic acid, selenium, self-heal, *Serenoa serrulata* extract, sericin, serine, sesame oil, *Sesamum indicum*, sesquioleate, Shao-yao, shea butter, *Siegesbeckia orientalis*, silica, silica dimethyl silylate, silicate, silicone, silk, silk powder, silk protein, siloxane, silt, silver, silver chloride, silver sulfadiazine, silver tip white tea leaf extract, *Silybum marianum* extract, simethicone, *Simmondsia chinensis*, sirtuins, skin respiratory factor, skin-identical ingredients, skin-repairing ingredients, skullcap extract, slip agent, slippery elm bark, soap, soapberry extract, soapwort, sodium acetate, sodium acrylate/acryloydimethyl taurate copolymer, sodium ascorbate, sodium ascorbyl phosphate, sodium benzoate, sodium bisulfite, sodium borate, sodium C14-16 olefin sulfonate, sodium carbomer, sodium carbonate, sodium carboxymethyl beta-glucan, sodium cetearyl sulfate, sodium chloride, sodium chondroitin sulfate, sodium citrate, sodium cocoamphoacetate, sodium cocoate, sodium cocoyl amino acids, sodium cocoyl glutamate, sodium cocoyl isethionate, sodium dehydroacetate, sodium dilauramidoglutamide lysine, sodium hexametaphosphate, sodium hyaluronate, sodium hydroxide, sodium hydroxymethylglycinate, sodium lactate, sodium lactobionate, sodium laureth sulfate, sodium laureth-13 carboxylate, sodium lauroamphoacetate, sodium lauroyl lactylate, sodium lauroyl sarcosinate, sodium lauryl glucose carboxylate, sodium lauryl sulfate, sodium metabisulfite, sodium methyl cocoyl taurate, sodium methyl taurate, sodium myreth sulfate, sodium palm kernelate, sodium palmate, sodium PCA, sodium PEG-7 olive oil carboxylate, sodium phytate, sodium polyacrylate, sodium salicylate, sodium silicate, sodium sulfite, sodium tallowate, sodium thioglycolate, sodium trideceth sulfate, *Solanum lycopersicum* extract, *Solanum tuberosum* extract, soluble fish collagen, solvent, Sonojell, sorbic acid, sorbitan oleate, sorbitan sesquioleate, sorbitan stearate, sorbitol, soy extract, soy isoflavones, soy oil, soy protein, soya sterol, spearmint oil, SPF, sphingolipids, spikenard, *Spiraea ulmaria*, spirulina, squalane, squalene, St. John's wort, star anise, steapyrium chloride, stearalkonium chloride, stearalkonium hectorite, stearates, steareth-20, stearic acid, stearyl alcohol, stearyl dimethicone, stearyl glycyrrhetinate, stearyl methicone, stem cells, strawberry begonia, styrax benzoin, styrene/acrylates copolymer, subtilisin, sucrose, sugarcane extract, sulfates, sulfur, sun protection factor, sunflower seed oil, sunscreens, superoxide dismutase, surfactant, sweet almond, sweet almond oil, *Symphytum officinale* extract, Szechuan peppercorn, talc, tallow, tamanu oil, *Tamarindus indica* seed extract, *Tanacetum parthenium*, tangerine oil, tannic acid, tannin, *Taraktogenos kurzii, Taraxacum officinale*, tartaric acid, Tazorac, TEA, tea tree oil, TEA-lauryl sulfate, teprenone, terephthalylidine dicamphor sulfonic acid, *Terminalia catappa, Terminalia sericea, Terminalia sericea* extract, tetradibutyl pentaerithrityl hydroxyhydrocinnamate, tetrahexyldecyl ascorbate, tetrahydrobisdemethoxycurcumin, tetrahydrobisdemethoxydiferuloylmethane, tetrahydrodemethoxycurcumin, tetrahydrodemethoxydiferuloylmethane, tetrahydrodiferuloylmethane, tetrahydromethoxycurcumin, tetrahydroxypropyl ethylenediamine, tetrasodium EDTA, tetrasodium etidronate, *Theobroma cacao* seed butter, thiamine HCL, thickening agent, thioctic acid, thiodipropionic acid, thioglycolate, thiotaurine, threonine, thyme extract, thyme oil, *thymus* hydrolysate, *Thymus serpillum* extract, *Thymus vulgaris, Thymus vulgaris* oil, *Tilia cordata*, Tinosorb M, Tinosorb S, tissue respiratory factor (TRF), titanium dioxide, tocopherol, tocopherol acetate, tocopheryl acetate, tocopheryl lineolate, tocotrienols, tomato extract, tormentil extract, tourmaline, tragacanth, tranexamic acid, transforming growth factor (TGF), trehalose, tretinoin, tribehenin, tribehenin PEG-20 esters, tricaprylin, triclosan, tridecyl salicylate, tridecyl stearate, tridecyl trimellitate, triethanolamine, triethoxycaprylylsilane, triethoxycaprylylsilane crosspolymer, triethoxysilylethyl polydimethylsiloxyethyl hexyl dimethicone, *Trifolium pratense*, triglyceride, *trigonella foenum-graecum* seed extract, trihydroxystearin, triisocetyl citrate, trilaurin, trimethylsiloxysilicate, trioclanolin, trioctanoin, trioctyldodecyl citrate, tripeptide-32, trisodium EDTA, *Triticum vulgare* (wheat) germ extract, *Triticum vulgare* oil, troxerutin, tryptophan, turmeric, *Tussilago farfara*, tyrosinase, tyrosine, ubiquinone, *Ulmus fulva* bark extract, ultramarines, *Ulva lactuca* extract, *Uncaria tomentosa* extract, *Undaria pinnatifida*, urea, *Urtica dioica*, UVA, *Uva ursi* extract, UVB, VA/crotonates, VA/crotonates copolymer, *Vaccinium macrocarpon* fruit extract, *Vaccinium myrtillus*, valine, *Vanilla planifolia* fruit extract, vascular endothelial growth factor (VEGF), verbena extract, vetiver oil or extract, vinyl dimethicone/methicone silsesquioxane crosspolymer, Viola tricolor extract, *Visnaga vera* extract, vitamin A, vitamin B1, vitamin B12, vitamin B2, vitamin B3, vitamin B5, vitamin B6, vitamin C, vitamin D, vitamin E, vitamin F, vitamin H, vitamin K, *Vitis vinifera, Vitreoscilla ferment*, volatile oil, VP/eicosene copolymer, VP/hexadecene copolymer, walnut extract, walnut oil, walnut-shell powder, water, watercress extract, watermelon fruit extract, wheat amino acids, wheat germ glycerides, wheat germ oil, wheat protein, whey, whey protein, white nettle, white oak bark extract, white tea leaf extract, white willow, wild ginger, wild yam extract, willow bark, willow herb, wintergreen oil, witch hazel, xanthan gum, xanthophyll, Xi xin, *Ximenia americana* oil, xylitol, xylose, xymenynic acid, yarrow extract, yeast, yeast extract, yellow 5, yellow 6 lake, yerba mate extract, ylang ylang, yogurt, yucca extract, *Yucca schidigera, Zanthoxylum piperitum*, zeolite, zinc, zinc carbonate, zinc gluconate, zinc oxide, zinc PCA, zinc phenolsulfonate, zinc stearate, zinc sulfate, *Zingiber officinale* roscoe, *Zingiber zerumbet*, Zingiberaceae, and *Zizyphus jujuba* fruit extract. In still another embodiment, the ingredient may be an antiseptic sic as sodium hypochlorite, quaternary ammonium componds, alcohols, betadine, iodine, and the like. In another embodiment, the ingredient may be a preservative such as gold, silver, PHMB, or sodium hypochlorite. For ingredients which are not water soluble one of skill in the art appreciates that appropriate use of a solvent will allow a non-water soluble ingredient to be used in accordance with the invention.

The active ingredient may also be one or more cationic biocides. Cationic biocides include quaternary ammonium compounds, bisbiguanides, and polymeric biguanides. The specific cationic biocides used in the invention include, but are not limited to, benzalkonium chloride, cetrimide, chlorhexidine, polihexanide biguanide (polihexanide, polyhexamethylene biguanide, polyhexamethylene guanide, poly (iminoimidocarbonyl-iminoimidocarbonyl-iminohexamethylene), poly(hexamethylenebiguanide), polyaminopropyl biguanide) and salts or combinations thereof.

In other embodiments, the petrolatum-based compositions described herein may comprise an active ingredient that stimulates healing. More specifically, the petrolatum-based compositions described herein may comprise a compound that stimulates healing alone or in addition to the active ingredients described above for use in intraoperative applications and chronic wound care applications. Non-limiting examples of compounds that stimulate healing include polycaprolactone-tricalcium phosphate (PCL-TCP), collagen, chitosan, cellulose, thrombin, chondroitin sulfate (CS), chondroitin sulfate succinimidyl succinate (CS-NHS), and growth factors such as TGF-alpha, TGF-beta (TGFβ1, TGFβ2, TGFβ3), platelet-derived growth factor (PDGF), epidermal growth factor (EGF), fibroblast growth factor also referred to as keratinocyte growth factor (FGF1, FGF2, FGF4, FGF7), vascular endothelial growth factor (VEGF), insulin-like growth factor (IGF), connective tissue growth factor (CTGF), activin, interleukin-1 (IL1α, IL1β3), TNFα, GM-CSF, or autologous intraoperative biologics such as platelet-rich plasma (PRP) and bone marrow (BM).

In other embodiments, the petrolatum-based compositions described herein may further comprise a dermatologically acceptable carrier. A "dermatologically-acceptable carrier," as used herein, is a component or components suitable for use in contact with human keratinous tissue without undue toxicity, incompatibility, instability, allergic response, and the like. Where employed, the carrier is inert in the sense of not bringing about a deactivation of the active ingredients, and in the sense of not bringing about any adverse effect on the skin areas to which it is applied. Common dermatological additives are also envisioned for some embodiments. In certain embodiments, a dermatological additive is a whitening agent and/or hemostatic agent.

The compositions described herein are a widely applicable delivery system for active ingredients. The compositions may be applied the desired site for delivery of the active ingredients. Generally, the application is topical to the skin, but the compositions may also be used intraoperatively. Additionally, the compositions may be incorporated in predetermined therapeutically effective amounts into disposables such as wipes, gauze, patches, wraps, bandages, adhesive strips, sponge, cotton swab, glove, sock, wrist bands, fabric, fibers, sutures, medication pad, underwear, tissue, pain-relief gel pack or bed liner and the like. For instance, the composition may be applied to the surface of, or impregnated into disposables.

II. Process for Making

The disclosure also provides a method for making the compositions described in Section (I). More specifically, the delivery system comprising a active ingredient is prepared by a method comprising: (a) dissolving the active ingredient in a solvent to give an active ingredient solution; (b) heating the petrolatum to a temperature sufficient to give a melted petrolatum, and heating the active ingredient solution to a temperature higher than the temperature of the petrolatum to give a heated active ingredient solution; (c) mixing the melted petrolatum and the heated active ingredient solution to give a melted mixture; and, (d) cooling the melted mixture to give the petrolatum-based composition. Steps (a)-(d) are conducted in a sequence.

The active ingredient, described in more detail below, is first dissolved in a solvent to give a active ingredient solution. Acceptable solvents for the active ingredient solution include water or other polar solvents. The active ingredient is typically dissolved in the solvent at a concentration ranging from about 0.05% to about 5%. Typically, the amount of solvent used is from about 1:10 to about 1:30 the amount of petrolatum and more preferably is about 1:20 to the amount of petrolatum by volume. The amount of active ingredient can be calculated by one skilled in the art to provide the desired weight percentage for the final composition. In one embodiment, an additional solvent such an alcohol is not needed. For some applications a small amount of organic solvent may be used to enhance solubility of the active ingredient.

Both the active ingredient solution and the petrolatum are heated. The heating of these two ingredients can be conducted at the same time or sequentially so long as the melted petrolatum and the heated active ingredient solution are at the appropriate temperatures during the mixing step. Petrolatum is a solid that melts at approximately 37° C. As such, petrolatum may be heated to any temperature at or above 37° C. For instance, the petrolatum may be heated to a temperature ranging from about 37° C. to about 45° C., from about 40° C. to about 50° C., from about 45° C. to about 55° C., from about 50° C. to about 60° C., from about 55° C. to about 65° C., from about 60° C. to about 70° C., from about 65° C. to about 75° C., from about 70° C. to about 80° C., from about 75° C. to about 85° C., from about 80° C. to about 90° C., from about 85° C. to about 95° C., or from about 90° C. to about 100° C. or more. Higher temperatures may also be envisioned. Preferably, the petrolatum is heated to a temperature ranging from about 37° C. to about 55° C., more preferably to a temperature ranging from about 40° C. to about 50° C. Heat may be provided to the petrolatum by any method known in the art, but a water bath or low temperature hot plate are preferred.

The active ingredient solution is heated to a temperature above the temperature of the melted petrolatum. Any temperature above the temperature of the melted petrolatum may be used in a method of the present disclosure, provided that the heat does not cause excessive degradation of an active ingredient or excessive evaporation of the active ingredient or polar solvent. For instance, the active ingredient solution may be heated to a temperature that is about 1° C. to about 10° C., about 5° C. to about 15° C., about 10° C. to about 20° C., about 15° C. to about 25° C., about 20° C. to about 30° C., about 25° C. to about 35° C., about 30° C. to about 40° C., about 35° C. to about 45° C., about 40° C. to about 50° C., about 45° C. to about 55° C., about 50° C. to about 60° C. or about 65° C. or about 75° C. higher than the temperature of the melted petrolatum. Higher temperatures may also be envisioned. Preferably, the active ingredient solution is heated to a temperature that is about 1° C. to about 10° C. higher than the temperature of the melted petrolatum. In another embodiment, the active ingredient solution is heated to a temperature that is about 1° C. to about 5° C. higher than the melted petrolatum. In still other embodiments, the active ingredient solution is heated to a temperature that is about 1° C., 2° C., 3° C., 4° C., or 5° C. above the temperature of the melted petrolatum. Again, the heating can be provided by any means known in the art but is preferably provided by a water bath or low temperature hot plate.

Once both the petrolatum and the active ingredient solution are heated as described above, the melted petrolatum and the active ingredient solution are mixed to give a melted mixture containing petrolatum and the heated active ingredient solution. The mixing can be accomplished by a variety of methods including homogenization, acoustic mixing, and high RPM mixing. Depending on the batch size, the size of the mixer, and the type of mixing, the mixing may be conducted for several minutes or more. When mixed in accordance with the parameters disclosed above, the melted petrolatum and the heated active ingredient solution fuse in the melted mixture.

After the melted petrolatum and the heated active ingredient solution have fused they are allowed to cool and solidify into the composition described more fully in Section (I) ("the final composition"). Cooling may be achieved by reducing the amount of heat provided to the melted mixture, or cooling may be achieved passively under conditions where no heating is added. In some embodiments, cooling is controlled so that the temperature of the melting mixture is gradually decreased to ambient temperatures. The product is preferably packaged a few degrees above its solidification point so that the packaging can be filled by pouring the melted mixture. The composition preferably solidifies to the final composition in the package. The package is sealed after this solidification.

The process may be conducted with two or more active ingredients. The active ingredients may be dissolved in solvent separately or may be dissolved in the same solvent. Additional active ingredients do not change the process steps above.

III. Methods of Use

In another aspect, the invention encompasses a method of delivering an active ingredient to a desired site.

In one embodiment, the compositions may be applied topically to a subject in need to deliver active ingredients to the skin. The subject is preferably human but the composition may also be useful in animals, for example domestic animals, livestock, or other types of animals. Application to the skin includes application to a wound site at any stage of healing. For example, the composition may be applied to the site of an abrasion, abscess, an arterial ulcer, the site of a burn, the site of debridement, a diabetic ulcer, dry or clotted blood, epithelial tissue, gangrene, a lesion, maceration, necrosis, rash, surgical incisions, and to wounds generally.

Alternatively, the compositions described herein may be used intraoperatively, or left internally at skin closure following surgery. The composition may also be used post-operatively as a topical dressing to deliver an active ingredient on a clean, closed site. The compositions described herein may also be useful in negative pressure wound therapy, hyperbaric oxygen therapy, and as a dressing for biologic skin substitutes. In negative pressure applications, the composition may be used to moisten sponges and dressings commonly used in negative pressure apparatuses. The composition may also be used as a personal lubricant or a lubricant for diagnostic uses. This list is intended to be exemplary and non-limiting.

In still another aspect, the invention encompasses a method of treating or preventing a skin condition using the composition described herein. The composition described herein may be applied topically to a subject in need. Specifically, the composition described herein may be applied topically to the skin of a subject in need. Subjects in need may be those with a skin condition. Subjects in need may also be subjects at risk for a skin condition. Non-limiting examples of skin conditions include acne, scarring, age-spots, dermatitis (contact dermatitis, photodermatitis, seborrheic dermatitis, nummular dermatitis, stasis dermatitis, dermatitis herpetiformis, atopic dermatitis, allergic dermatitis), cold sores, skin discoloration, eczema, rosacea, psoriasis, warts, blisters, chafing, sunburn, rash, hives wrinkling, sagging, photodamaged skin, sensitive skin, dry skin, rough skin, flaky skin, red skin, irritated skin, and itchy skin. This list is intended to be exemplary and non-limiting.

The amount of composition applied in the methods described herein can and will vary depending on the condition being treated and the severity of that condition. Generally, the amount used is sufficient to cover the affected skin area with a thin layer of the composition. The composition is applied directly to the skin. In some embodiments, the composition is spread so that it forms a thin layer over the treatment area. In other embodiments, the composition is spread by a melting action that occurs as the warmth of the patient's skin melts the petrolatum. The composition may be covered with a bandage after application. The composition may also be coated on or impregnated in a dressing, such as, for example, a bandage.

The composition when applied to the skin is non-irritant and non-cytotoxic. These properties allow the composition to be used on sensitive areas such as wounds that have recently been debrided. These characteristics also allow for delivery of the active ingredient over a long period, such as for example 2 weeks, 4 weeks, 6 weeks, 8 weeks, or longer without irritation to the treated area. It will be recognized however, that the compositions may be used for shorter periods of time if necessary.

The compositions are also capable of extended release of the active ingredient to the area of application. "Extended release" as used herein means that the compositions release active ingredients to the application site over a period of time extending past twelve hours. The time over which the extended release is provided is variable depending on the amount of the composition that is applied and on the heat of the wound, but in general, the release of active ingredients is extended beyond the initial application and active ingredients have been shown to be released for up to 1 week. This extended release allows the composition to be applied less frequently and improves patient compliance with the treatment.

The compositions of the invention also offer kinetic release when applied to the skin. Kinetic release means that the active ingredients are released to the treatment area more rapidly when the treatment area is hotter. Kinetic release can be particularly useful in treatment of infections with an antimicrobial active ingredient. Because more serious infections are hotter than less serious infections, kinetic release provides more active ingredients rapidly to the worst infections, thereby facilitating their treatment.

In still another embodiment, the invention provides a petrolatum-based composition comprising petrolatum and an active ingredient prepared by steps comprising: a) dissolving the active ingredient in a solvent to give an active ingredient solution; b) heating the petrolatum to a temperature sufficient to cause the petrolatum to melt to give a melted petrolatum and heating the active ingredient solution to a temperature higher than the temperature of the melted petrolatum to give a heated active ingredient solution; c) mixing the melted petrolatum and the heated active ingredient solution to give a melted mixture; and d) cooling the melted mixture to give the petrolatum-based composition.

EXAMPLES

The following examples are included to demonstrate preferred embodiments of the disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1. Exemplary Formulation Process

"Formulation 1" (FIG. 1) was prepared by adding 2540.3 pounds of white petrolatum to a tank that has been cleaned and sterilized in accordance with SOP protocol. In the tank was used to heat the petrolatum to 110° C.-113° F. to melt the petrolatum. In a separate clean and sanitized container 133.70 pounds of water and the desired amount of BZK and PHMB were added and heated to 122° F. When both phases are at temperature, the solution phase was slowly added to the petrolatum with mixing. The heat was decreased slowly to 96-104° F. The product was tested for quality control and transferred to polypropylene drums. The resulting composition was shiny and white to slightly yellow in appearance. Specific gravity at 25° C. matches specification when it is from 0.830-0.910. Viscosity at @25° C. TF @10 rpm matches specification when it is from about 225,000-300,000 cps. The final formulation contained the following ingredients by weight percent: 95% petrolatum; 0.13% BZK, 0.2% PHMB, and 4.67% water.

Example 2. Skin Sensitization Evaluation

A study was conducted on the formulation of Example 1, referred to herein as "Formulation 1" to assess skin sensitization. Patches comprising Formulation 1 were affixed directly to the skin of 53 human study participants representing an age range from 18-63 and five skin types. Table 1 presents the participant demographics. Patches remained in place for 48 hours after the first application. Participants were instructed not to remove the patches prior to their 48 hour scheduled visit. Thereafter, the subjects were instructed to remove patches for 24 hours. This procedure was repeated until a series of nine consecutive, 24 hour exposures had been made three times per week for three consecutive weeks. Test sites were evaluated by trained personnel. Following a 10-14 day rest period, a retest/challenge dose was applied once to a previously unexposed test site. Test sites were evaluated by trained personnel 48 and 96 hours after application. The sites were scored based on the International Contact Dermatitis Research Group scoring scale (Rietschel, Fowler, Ed., Fisher's Contact Dermatitis (fourth ed.). Baltimore, Williams & Wilkins, 1995) as presented in Table 2.

TABLE 1

Participant Demographics.

| | |
|---|---|
| Number of subjects enrolled | 53 |
| Number of subjects completing study | 53 |
| Age Range | 18-63 |
| Sex | Male 13 |
| | Female 40 |
| Fitzpatrick Skin Type* | |
| 1 - always burn, does not tan | 0 |
| 2 - burn easily, tan slightly | 4 |
| 3 - burn moderately, tan progressively | 47 |
| 4 - burn a little, always tan | 2 |
| 5 - rarely burn, tan intensely | 0 |
| 6 - never burn, tan very intensely | 0 |

*Agaghe P, Hubert P. Measuring the skin. (p. 473, table 48.1) Springer-Verlag Berlin Heidelberg, 2004.

TABLE 2

Scoring Scale.

| | |
|---|---|
| 0 | No reaction (negative) |
| 1 | Erythema throughout at least ¾ of patch area |
| 2 | Erythema and induration throughout at least ¾ of patch area |
| 3 | Erythema, induration and vesicles |
| 4 | Erythema, induration and bullae |
| D | Site discontinued |
| Dc | Subject discontinued |

No adverse reactions of any kind were reported during the course of study. Accordingly, Formulation 1 gives no identifiable signs or symptoms of primary irritation or sensitization (contact allergy).

Example 3. Antimicrobial Efficiency Testing

Antimicrobial efficacy testing was conducted according to USP 51. Five microbes were tested. Each organism was inoculated at an inoculum level of 1×10$^6$ colony forming units (CFU) per gram for bacteria or 1×10$^5$ CFU per gram for yeast and mold. The inoculated samples were then stored at 20-25° C. for 28 days. The population of each microorganism was determined by plate counting at Day 2, 7, 14, 21, and 28. The plate counts were performed at a 1:10 initial dilution using Modified Letheen Broth as the diluent and plated onto Tryptic Soy and Sabouraud Dextrose agar.

A single application of Formulation 1 gave 100% elimination from day 2 to day 28 for all microbes tested (Table 3). Given the 100% elimination, there was a 4 log reduction in the yeast/mold species and a 5 log reduction in the bacterial species (Table 4). Table 5 is a positive control indicating that the method used recovers 80-100% of the microbe in the absence of Formulation 1. Accordingly, the microbes present in the test sample were eliminated under the tested conditions. The results illustrate the broad spectrum of activity for Formulation 1.

TABLE 3

Preservative Testing.

| | Colony Forming Units/gram | | | | | |
|---|---|---|---|---|---|---|
| Organism | Inoculum/g | Day 2 | Day 7 | Day 14 | Day 21 | Day 28 |
| *Staphylococcus aureus* (bacteria) ATCC#6538 | 1 × 10$^6$ | <10 | <10 | <10 | <10 | <10 |
| *Pseudomonas aeruginosa* (bacteria) (ATCC#9027) | 1 × 10$^6$ | <10 | <10 | <10 | <10 | <10 |
| *Escherichia coli* (bacteria) (ATCC#8739) | 1 × 10$^6$ | <10 | <10 | <10 | <10 | <10 |
| *Candida albicans* (yeast) (ATCC#10231) | 1 × 10$^5$ | <10 | <10 | <10 | <10 | <10 |
| *Aspergillus niger* (mold) (ATCC#16404) | 1 × 10$^5$ | <10 | <10 | <10 | <10 | <10 |

TABLE 4

Log Reduction Calculation from Initial Inoculum.

| | 14 days | 28 days |
|---|---|---|
| *Aspergillus niger* | 4.00 | 4.00 |
| *Candida albicans* | 4.00 | 4.00 |
| *Pseudomonas aeruginosa* | 5.00 | 5.00 |
| *Escherichia coli* | 5.00 | 5.00 |
| *Staphylococcus aureus* | 5.00 | 5.00 |

TABLE 5

Preservative Testing Validation.

| Organism | Inoculum | Dilution | Microbial Recovery | Diluent | Percent Recovery |
|---|---|---|---|---|---|
| *Staphylococcus aureus* | 76 cfu/plate | 1:10 | 69 cfu/plate | LB | 87% |
| *Pseudomonas aeruginosa* | 83 cfu/plate | 1:10 | 81 cfu/plate | LB | 97% |
| *Escherichia coli* | 68 cfu/plate | 1:10 | 58 cfu/plate | LB | 85% |
| *Candida albicans* | 63 cfu/plate | 1:10 | 50 cfu/plate | LB | 79% |
| *Aspergillus niger* | 60 cfu/plate | 1:10 | 60 cfu/plate | LB | 100% |

CFU = colony forming units;
LB = Letheen Broth;
Diluent = Letheen Broth;
Dilution: 1:10

Example 4: Cytotoxicity Evaluation

The study was conducted to assess the biological reactivity of mammalian cells (grown in culture) to the agar-diffusible elements of Formulation 1.

The samples to be evaluated for cytotoxicity include test product comprising Formulation 1, Amber latex tubing as a positive control, and HDPE sheet stock as a negative control. The samples were sized to have no less than 100 mm$^2$ of contact surface and provide coverage of approximately 10% of the test dish. The dimensions of the test product comprising Formulation 1 were 1.1×1.1-1.2 cm; the dimensions of the positive control were 1.0×2.55-2.7 cm; and the dimensions of the negative control were 1.15×1.0-1.2 cm. The manipulation of the samples was performed aseptically.

Prior to exposure to the samples, the L929 Mouse Fibroblast cells were subcultured in Minimum Essential Medium (MEM) with 10% Fetal Bovine Serum (FBS) to achieve a confluency of approximately 80±10% at the time of exposure. The cells were examined for normal morphology and the absence of contamination. Once the cells met the acceptance criteria for use, individual dishes were numbered in triplicate to represent the controls and the test product comprising Formulation 1.

On the day of testing, the subculture media was carefully removed from each test dish and replaced with a 2 mL aliquot of the 1:1 overlay medium (in equal parts of 2× Minimum Essential Medium (with 2% Fetal Bovine Serum) and Agar Noble). After allowing the overlay medium to solidify, a single test product comprising Formulation 1 or control sample was placed in the center of each dish (in contact with the agar surface). Triplicate cultures were prepared for each test product comprising Formulation 1 and positive and negative controls (one sample per dish). When the test product comprising Formulation 1 or positive/negative control has only one face designated for patient-contact, that "side" of the sample was directed toward the agar. The test dishes, along with 3 dishes with overlay medium only (Monolayer Negative Controls), were then placed in the 37° C./5% CO$_2$ incubator to initiate the exposure interval.

The dishes were incubated for 24 hours and then microscopically examined for an indication of cellular response. A preliminary microscopic examination of the cells was made prior to staining and before the control and test product comprising Formulation 1 were removed from the agar layer. The cells were then stained with a fresh working Neutral Red Solution to facilitate response grading. The test product comprising Formulation 1 and control samples were removed from the dishes at this time. The stained cells were then fixed by the addition of buffered formalin. Following fixation, the agar overall was removed from each dish. Following staining, the cellular responses were then evaluated microscopically and macroscopically (by examining the dishes against a white surface) and the results were recorded.

For the control samples to be deemed valid, the negative controls may be no greater than Grade 0 and the positive control may be no less than Grade 3. For the test product comprising Formulation 1, a Grade of 0, 1 (slight) or 2 (mild) indicates the test product comprising Formulation 1 "meets" the assay acceptance criteria and a Grade of 3 (moderate) or 4 (severe) indicates the test product comprising Formulation 1 does not meet the assay acceptance criteria. Table 6 depicts the Grading guidelines.

TABLE 6

Grading Guidelines.

| Grade(1) | Reactivity | Description of the Reactivity Zone(2) |
|---|---|---|
| 0 | None | No detectable zone around or under specimen |
| 1 | Slight | Some malformed or degenerated cells under specimen(3) |
| 2 | Mild | Zone limited to area under specimen |
| 3 | Moderate | Zone extends 0.45 to 1.0 cm beyond specimen |
| 4 | Severe | Zone extends greater than 1.0 cm beyond specimen |

(1)The use of the above Grading Table is contingent on the test article meeting the minimum surface area requirements of ≥100 mm². Should samples of smaller dimensions be tested, the reactivity (if any) would be expected to be less and the grading would need to be justified.
(2)The extent of the Reactivity Zone is the maximum measured distance from the edge of the specimen to the margin of monolayer where degenerated cells are no longer observed. Where described as "under specimen", this maximum measured distance is limited to <0.45 cm beyond the specimen.
(3)To be interpreted as "slight" reactivity, no more than 50% of the cells under the specimen may exhibit reactivity as rounding and/or lysis.

Table 7 depicts the results of the study. The assay controls met the acceptance criteria for a valid assay. All negative controls responses were no greater than Grade 0 and the positive control response were not less than Grade 3. The responses observed for the test product comprising Formulation 1 were interpreted according to the current USP guidelines. The Grade 1 response from the test product comprising Formulation 1 is considered to be "non-cytotoxic" (i.e. meets ISO test acceptance requirements of no more than Grade 2 reactivity). Accordingly, Formulation 1 does not damage mammalian cells.

TABLE 7

Study Results.

| | | | Macroscopic Reading (Zone Dimensions) | Microscopic Reading (% Rounded/Lysed) | Grade |
|---|---|---|---|---|---|
| Monolayer Negative Control | | 1 | No detectable zone | 0%/0% | 0 |
| | | 2 | No detectable zone | 0%/0% | 0 |
| | | 3 | No detectable zone | 0%/0% | 0 |
| Material Positive Control | | 1 | Clear Zone 3.2 × 3.2; Greatest distance from specimen 1.5 cm | 100%/100% | 4 |
| | | 2 | Clear Zone 3.2 × 3.2; Greatest distance from specimen 1.5 cm | 100%/100% | 4 |
| | | 3 | Clear Zone 3.2 × 3.2; Greatest distance from specimen 1.5 cm | 100%/100% | 4 |

TABLE 7-continued

Study Results.

| | | Macroscopic Reading (Zone Dimensions) | Microscopic Reading (% Rounded/Lysed) | Grade |
|---|---|---|---|---|
| Material Negative Control | 1 | No detectable zone | 0%/0% | 0 |
| | 2 | No detectable zone | 0%/0% | 0 |
| | 3 | No detectable zone | 0%/0% | 0 |
| Test Product Comprising Formulation 1 | 1 | Entire dish lightly stained ~5% rounded directly under sample | 1.5%/1.5% | 1 |
| | 2 | Entire dish lightly stained ~5% rounded directly under sample | 1.5%/1.5% | 1 |
| | 3 | Entire dish lightly stained ~5% rounded directly under sample | 1.5%/1.5% | 1 |

Example 5: Rabbit Skin Irritation

The study was conducted to assess the irritating potential of Formulation 1 to produce dermal irritation.

Figure 2:
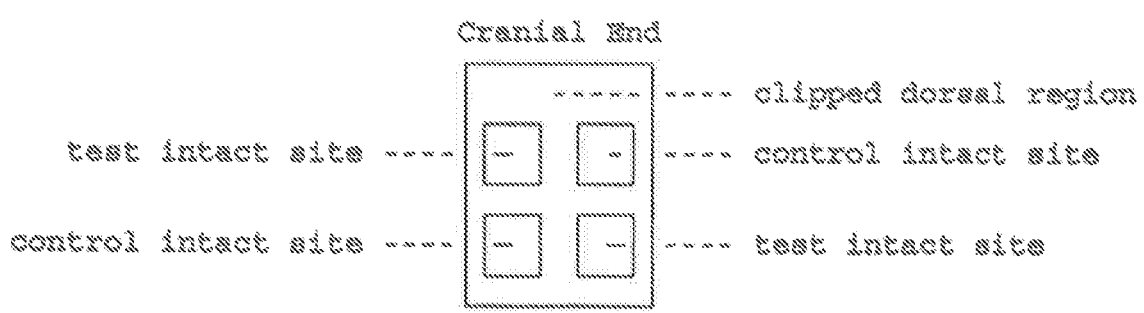
FIG. 2 depicts a schematic of the arrangement of test and control sites in the rabbit skin irritation study.

Within 24 hours to 4 hours before test application, the backs of female albino New Zealand White rabbits were clipped free of hair, exposing 2 test and 2 control areas on each side of the spine with a size of approximately 15 cm×15 cm. The two test sites are located on the left cranial section and the right caudal section of the dorsal region. The two control sites are located on the left caudal and right cranial section of the dorsal region. FIG. 2 depicts the arrangement of test and control sites. The exposed skin is wiped with alcohol and dried. Rabbits of acceptable skin quality were selected and used for testing.

A 25×25 mm gauze patch saturated with 0.5 mL (liquid) or 0.5 g (powder) of Formulation 1 is applied to the clipped test sites. A 25×25 mm gauze patch saturated with 0.5 mL of 0.9% NaCl is used for the control and applied to the clipped control sites. The patches are secured using hypoallergenic, waterproof, surgical tape over the test and control sites. The animal's trunk is securely wrapped so as to maintain the position of the patches. Patches are left applied for a minimum of four hours.

After patch removal, the test and control sites were then scored for erythema and edema at 1, 24, 48 and 72 hours after patch removal. Only the 24, 48, and 72 hour observations were scored and used for calculations. The criteria for scoring is presented in Table 8. If no response was expected, testing was conducted using three animals per test article. If irritation was anticipated, one animal was tested initially. If the first animal received a score of 2 or less for either erythema or edema, 2 additional rabbits were used to conclude the test.

TABLE 8

Scoring Criteria for Test Reactions.

| Reaction | Description | Score |
|---|---|---|
| Erythema (ER) | No erythema | 0 |
| | Very slight (barely perceptible) | 1 |
| | Well defined | 2 |
| | Moderate | 3 |
| | Severe (beet-redness) to eschar formation preventing grading of erythema | 4 |
| Edema (ED) | No edema | 0 |
| | Very slight (barely perceptible) | 1 |

TABLE 8-continued

Scoring Criteria for Test Reactions.

| Reaction | Description | Score |
|---|---|---|
| | Well-defined edema (edges of area well-defined by definite raising | 2 |
| | Moderate (edges raised ~1 mm) | 3 |
| | Severe (raised more than 1 mm and extending beyond exposure area) | 4 |

For each animal and each extract, when applicable, the scores for the test article comprising Formulation 1 for erythema and edema at each time were added. This total was divided by the total number of observations. The same was done for the control sites. The control result was subtracted from the test results to give the irritation index for each animal. These scores for each animal were added and divided by the total number of animals to give the Primary Irritation Index. The Primary Irritation Index is depicted in Table 9. For any response, the Maximum Irritation Response, the time of onset of the response and the time of maximum response was recorded.

TABLE 9

Primary Irritation Index

| Primary Irritation Index | Response Category |
|---|---|
| 0-0.4 | Negligible |
| 0.5-1.9 | Slight |
| 2-4.9 | Moderate |
| 5-8 | Severe |

The results indicated that the skin reactions for both the test article comprising Formulation 1 and control samples were not significant. That data is presented in Table 10 below. Accordingly, the Formulation 1 is non-irritating.

TABLE 10

Direct Application of Test Article.

| | Formulation 1 | Control |
|---|---|---|
| Rabbit No. 14384 | ER + ED = Total<br>0 0 0 | ER + ED = Total<br>0 0 0 |
| | Test Total − Control Total = 0 | |
| | Total Score Average = 0 | |
| Rabbit No. 14387 | ER + ED = Total<br>0 0 0 | ER + ED = Total<br>0 0 0 |
| | Test Total − Control Total = 0 | |
| | Total Score Average = 0 | |
| Rabbit No. 14394 | ER + ED = Total<br>0 0 0 | ER + ED = Total<br>0 0 0 |
| | Test Total − Control Total = 0 | |
| | Total Score Average = 0 | |
| Total Average (0) = 0 Primary Irritation Index | | |
| No. of Animals (3) | | |

To positively validate the test, 10% sodium dodecyl sulfate (SDS), which is a known dermal irritant, in petroleum jelly was applied to a 2.5 cm×2.5 cm gauze patch. As a negative control, 0.5 mL of 0.9% NaCl was applied to a 2.5 cm×2.5 cm gauze patch. A Primary Irritation Index in the moderate to severe range is considered a positive result. The test system and methods utilized were the same as described above. Table 11 presents the results validating the study.

TABLE 11

Primary Skin Positive Validation Test.

| | 10% SDS | Control |
|---|---|---|
| Rabbit No. 14279 | ER + ED = Total<br>18 14 32 | ER + ED = Total<br>0 0 0 |
| | Test Total − Control Total = 32 | |
| | Total Score Average = 5.3 | |
| Rabbit No. 14280 | ER + ED = Total<br>21 19 40 | ER + ED = Total<br>0 0 0 |
| | Test Total − Control Total = 40 | |
| | Total Score Average = 6.6 | |
| Rabbit No. 14281 | ER + ED = Total<br>23 21 44 | ER + ED = Total<br>0 0 0 |
| | Test Total − Control Total = 44 | |
| | Total Score Average = 7.3 | |
| Total Average (19.3) = 6.4 Primary Irritation Index | | |
| No. of Animals (3) | | |

Example 6. Suspension Time-Kill Procedure for MRSA, *T. rubrum*, and *Staphylococcus epidermidis*

A study was conducted to evaluate the changes in the population of MRSA in an antimicrobial liquid suspension comprising Formulation 1. Methicillin-resistant *Staphylococcus aureus* (MRSA) is a Gram-positive, cocci shaped, aerobe which is resistant to the penicillin-derivative antibiotic methicillin. MRSA can cause troublesome infections, and their rapid reproduction and resistance to antibiotics makes them more difficult to treat. MRSA bacteria are resistant to drying and can therefore survive on surfaces and fabrics for an extended period of time and therefore makes this bacteria an excellent representative for antimicrobial efficacy testing on surfaces.

Figure 3:
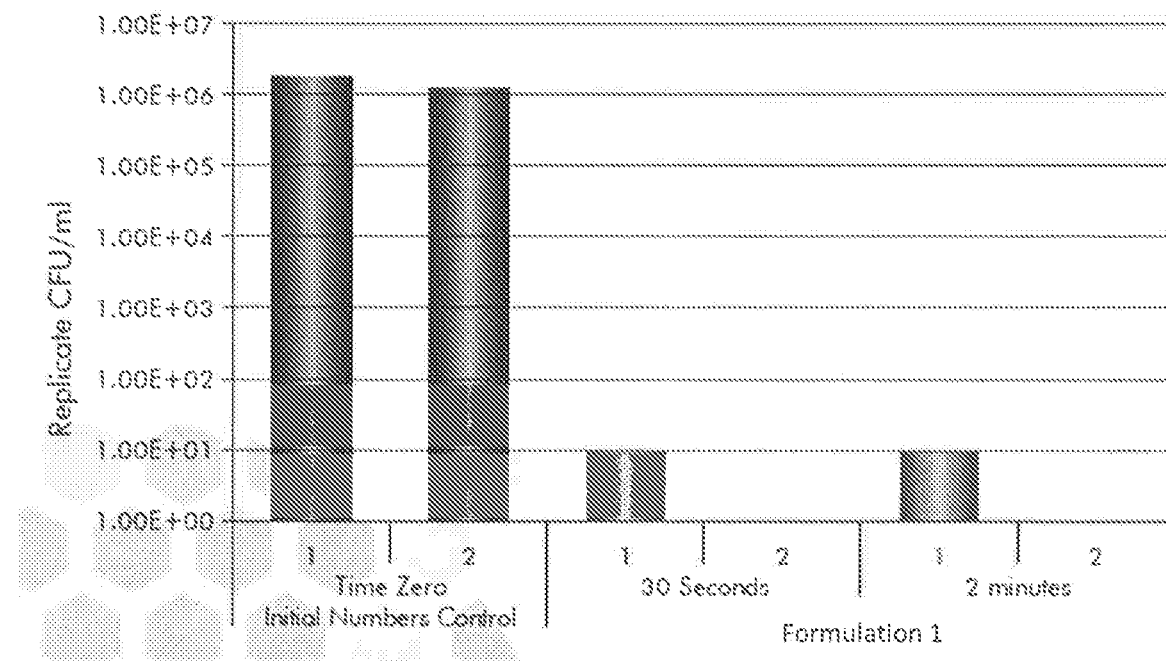
FIG. 3 depicts a graph showing the reduction of MRSA in the presence of Formulation 1 in the suspension time-kill procedure.

To conduct the study, MRSA was prepared in liquid culture medium (Letheen Broth). The suspension of MRSA was standardized by dilution to $10^6$ in a buffered saline solution. Formulation 1 and control substance (PBS) were dispensed in identical volumes to sterile vessels. Independently, Formulation 1 and control substance were each inoculated with MRSA, then mixed and incubated. Control substances were immediately harvested and represented the concentration present at the start at the test (i.e. time zero). At the conclusion of contact time, a volume of the liquid test product was harvested and chemically neutralized. Dilutions of the neutralized test solution were assayed using appropriate growth media to determine the surviving MRSA at the respective contact times. Reductions in MRSA were calculated by comparing initial microbial concentrations to final microbial concentrations. Table 12 and FIG. 3 present the results of the study.

TABLE 12

Results of Suspension Time-Kill Test for MRSA (33592)

| Test substance | Contact time | Replicate | Replicate CFU/ml* | Average CFU/ml | Percent Reduction vs. Control at Time Zero | Log$_{10}$ Reduction vs. Control at Time Zero |
|---|---|---|---|---|---|---|
| PBS | Time Zero | 1 | 1.75E+06 | 1.48E+06 | N/A | |
| | | 2 | 1.20E+06 | | | |
| Formulation 1 | 30 seconds | 1 | 1.00E+01 | <1.00E+01 | >99.9993% | >5.17 |
| | | 2 | <1.00E+01 | | | |
| | 2 minutes | 1 | 1.00E+01 | <1.00E+01 | >99.9993% | >5.17 |
| | | 2 | <1.00E+01 | | | |

*The limit of detection for the assay is 1.00E+01 CFU/ml. Values below the limit of detection are notes as <1.00E+01 in the table.

The same study was conducted with *Trichophyton rubrum*. *T. rubrum* is a fungus which belongs to the dermatophyte group. Dermatophytes commonly cause skin disease in animals and humans. *T. rubrum* is anthropophilic, meaning it preferentially infects humans over animals. This parasite is the most common cause of fungal infection of the fingernail and Athlete's foot, this specific strain was isolated from a human toenail. In the laboratory, visible colonies can be observed after approximately 4-5 days and are fluffy and white in appearance. *T. rubrum* is a popular test microorganism for fungicidal testing, especially for products intended for use in environments where skin infections can occurs and spread rapidly such as locker rooms and schools.

Figure 4:
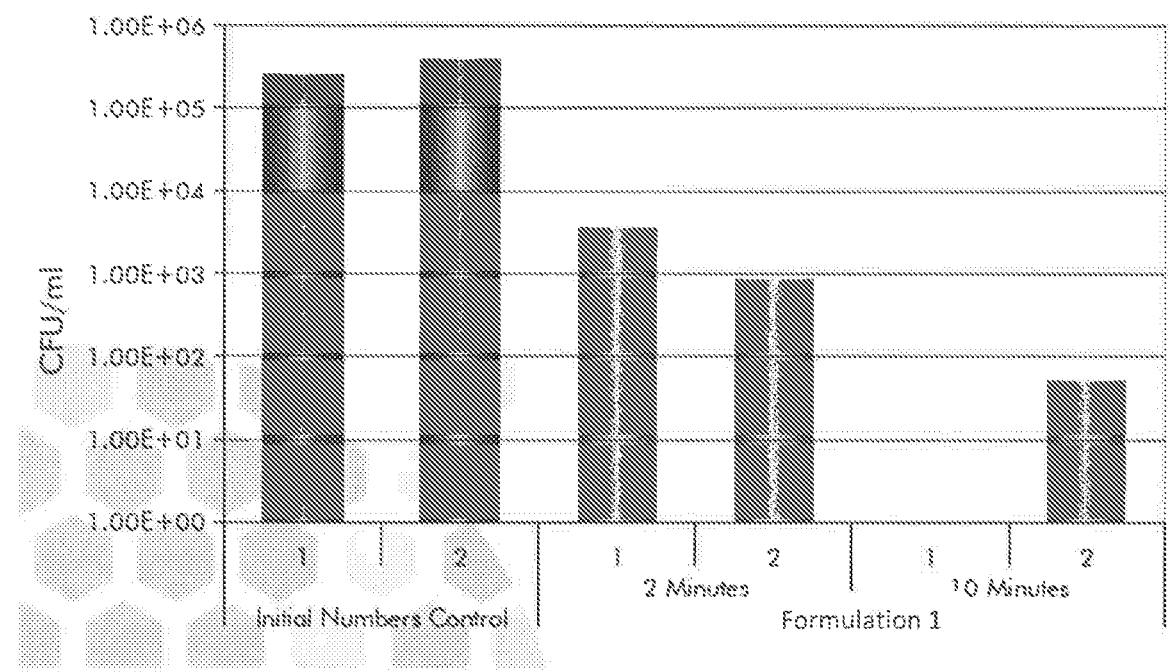
FIG. 4 depicts a graph showing the reduction of T. rubrum in the presence of Formulation 1 in the suspension time-kill procedure.

To conduct the study, *T. rubrum* was prepared on agar (potato dextrose agar). The *T. rubrum* was resuspended and inoculated at a dilution of ~$10^6$ into vessels containing Formulation 1 and control substance (PBS). Control substances were immediately harvested and represented the concentration present at the start at the test (i.e. time zero). At the conclusion of contact time (2 or 10 minutes), a volume of the liquid test product was harvested and chemically neutralized. Dilutions of the neutralized test solution were assayed using appropriate growth media to determine the surviving *T. rubrum* at the respective contact times. Reductions in *T. rubrum* were calculated by comparing initial microbial concentrations to final microbial concentrations. Table 13 and FIG. 4 present the results of the study.

TABLE 13

Results of Suspension Time-Kill Test for *T. rubrum* (MYA-4438)

| Test substance | Contact time | Replicate | Replicate CFU/ml* | Average CFU/ml | Percent Reduction vs. Control at Time Zero | Log$_{10}$ Reduction vs. Control at Time Zero |
|---|---|---|---|---|---|---|
| PBS | Time Zero | 1 | 2.55E+05 | 3.15E+05 | N/A | |
| | | 2 | 3.75E+05 | | | |
| Formulation 1 | 2 minutes | 1 | 3.50E+03 | 2.18E+03 | 99.31% | 2.16 |
| | | 2 | 8.50E+02 | | | |
| | 10 minutes | 1 | <5.00E+01 | <5.00E+01 | >99.98% | >3.80 |
| | | 2 | 5.00E+01 | | | |

*The limit of detection for the assay is 5.00E+01 CFU/ml. Values below the limit of detection are notes as <5.00E+01 in the table.

The same study was conducted with *Staphylococcus epidermidis*. Gram-positive organisms currently account for 50-60% of nosocomial bacteremic events. *Staphylococcus epidermidis* is the most common gram-positive organism isolated from blood (30% of isolates) and accounts for the majority of infections that are associated with intravascular catheters, as it is capable of forming antibiotic resistant biofilms on plastic surfaces.

In an effort to further explore the preventative benefits of Formulation 1 in preventing catheter related and hospital acquired infections, a suspension time kill assay as described above was initiated on this often under-discussed organism. A nearly 7 log kill over 24 hours was observed, which represents a typical change interval for intravenous catheter dressings (Table 14).

TABLE 14

Results of Suspension Time-Kill Test for *S. epidermidis* (ATCC 12228)

| Test substance | Contact time | Replicate CFU/ml* | Percent Reduction vs. Control at Time Zero | Log$_{10}$ Reduction vs. Control at Time Zero |
|---|---|---|---|---|
| PBS | Time Zero | 4.80E+06 | N/A | |
| Formulation 1 | 24 Hours | <1.00E+00 | >99.99998% | >6.68 |

The limit of detection is 1.00E+00 and is represented as <1.00E+00.

Example 7. the Use of Formulation 1 in a Slow Healing Wound Complicated by Patient Non-Compliance: Case Report A 56-year-old black male presented to clinic with the chief complaint of venous ulcers of right dorsal and plantar surfaces of foot and 2nd and 3rd toes. He had a prior medical history significant for chronic lymphedema, DM, HTN, Hyperlipidemia, CVA with residual hemiparesis of right side, wheelchair bound, tobacco dependence, seizure disorder, depression and asthma. He had been treated in the past with butadiene gauze wraps and iodasorb with kling, ace, and coban wraps with little improvement. Wound care was delivered twice weekly.

The patient received Clindamycin 300 TID×7 days due to the markedly minimal improvement of wound status over the first 7 weeks of treatment. Minimal improvement was noted after the antibiotic course.

Formulation 1 was utilized for the first time. A thin layer was applied to affected limb and ulcerations. The limb was dressed with gauze and coban in a compression wrap with weekly dressing changes to follow in this manner. Twenty-one days later significant improvement in wound appearance was observed and the wound on dorsal surface of the right foot had resolved completely. By four weeks, the entire dorsal surface was resolved and wounds were limited to plantar surface of the right 2nd and 3rd toes. By two months, wounds on plantar surfaces of the right foot were very defined and without any maceration. By three months, wounds had become essentially dry eschars with all tissues fully epithelialized.

In summary, all previous attempts to treat the patient's extensive wounds had failed but the introduction of Formulation 1 to the treatment marked a significant turning point in his care. Even in the face of extensive non-compliance and extended dressing change intervals, Formulation 1 remained in contact with the wound and continued to manage the environment.

Example 8. Use of Formulation 1 in Patient with History of Delayed Healing: Case Report A 76-year-old white female presented to clinic 24 hours after sustaining a 1.0×5.0×0.1 mm laceration to her right shin. She relates that she was standing near a wood pile when some wood fell and cut her. Radiographs were negative for fracture and ultrasound found no evidence of retained foreign body. The wound did not probe to bone. Her tetanus status was brought up to date. The wound was cleaned with sterile saline, edges re-approximated, and closed with retaining sutures and simple closure sutures in local ER.

Patient's medical history was significant for diabetes mellitus type 2 insulin dependent, CKD-4, ASCVD, and CABG-4 vessel. Notably, she relates a history of poor and delayed wound healing from graph site of right lower limb which took over 3 months to heal. She also suffers from peripheral neuropathy HTN, hyperlipidemia, obesity, and PVD/PAD.

Patient was seen in clinic and expressed concerns due to her history of delayed healing. Formulation 1 was applied with a standard dry, sterile dressing. Patient was instructed to return weekly for dressing changes.

The simple sutures were removed 2 weeks later. The wound showed no signs of dehiscence or infection. Edges were well approximated and surrounding tissue was appropriate to temperature and color. Formulation 1 continued to be used exclusively.

Retaining sutures were removed a week later. The wound was showing progressing epithelialization and had significantly decreased in size. The wound was dressed with Band-Aid and Formulation 1 for home use until completely healed.

By week 4, the patient was healed. There were no issues with wound healing or closure in a patient who had previously taken 12 weeks to heal from a saphenous graph harvest site. No revascularization had been done nor had any other health factor changed since the graft. This indicates that the use of Formulation 1 played an integral role in the closure of this wound.

The only factor that was changed in the patient's wound care for this laceration was the introduction of topical Formulation 1. With use of this product, the patient showed no signs of delayed healing. Her wound granulated and epithelialized as would be expected of a person without multiple systemic diseases. Formulation 1 appeared to have facilitated non-delayed healing while keeping the wound environment moist without macerating. Additionally, Formulation 1 stayed in contact with the wound and effective for a week without requiring dressing change, which is a benefit for patients with limited resources and transportation difficulties.

Example 9. Postoperative Treatment *Streptococcus* B Perianal Abscess with Formulation 1: Case Report A 51-year-old woman was admitted for the management of a perianal abscess. The patient had a history of a prior perianal abscess 6 months previously and an iodine allergy. The prior abscess had been treated via bedside I&D and oral antibiotics. With the recurrence of infection, concern for the presence of an anal fistula arose and the patient was admitted under SIRS criteria for evaluation and intervention.

Parenteral antibiotics were initiated, she was taken to the operating room for definitive treatment and placed under MAC anesthesia. An I&D was performed and exploration of the perianal space revealed a transsphincteric fistula as the source of the infection. A seton was initially placed to delineate the fistula. The fistula was subsequently repaired after the abscess was drained and washed out. Post-operatively a 3.3 cm deep soft tissue deficit remained.

In light of the patient's iodine allergy, the wound could not be treated with the standard betadine treated packing strips. Instead, the wound was packed with plain packing strips treated with Formulation 1, gauze, and sealed with Tegaderm. The patient was discharged on oral antibiotics with instructions for daily dressing changes to be performed.

Daily packing changes with the Formulation 1-treated packing strips were performed. By day 10 the soft tissue defect had fully granulated and packing was discontinued. The wound was subsequently dressed with a thin layer of Formulation 1 applied to the peri-wound area, with gauze and Tegaderm to seal the peripheral edges. By day 17 wound closure had been achieved.

The rate of granulation was markedly improved with the use of Formulation 1 when compared with the rates of healing with betadine packing strips. Typical rates with betadine strips run in the 4-6-week range. The difference in the rate of granulation is attributed to the difference in cytotoxic properties of the two products. Betadine, while being bactericidal, is also cytotoxic to fibroblasts which delays healing. Formulation 1 combines bactericidal properties with non-cytotoxicity to allow a more ideal environment for healing.

This case highlights the importance using of a non-cytotoxic, anti-microbial packing in the treatment of post-operative wounds. Ultimately, shorter duration of healing reduces the likelihood of opportunistic post-op infection and the use of a topical anti-microbial as an adjunctive treatment in conjunction with oral antibiotics provides a more ideal setting for healing to take place.

Example 10. the Use of Formulation 1 in the Treatment of Severe Abrasions: Case Report A 22-year old healthy male with no comorbidities was admitted to the emergency room with 2nd degree abrasions secondary to a locker room injury. Patient's tetanus status was addressed and wounds were cleaned and dressed with triple-antibiotic ointment, sterile gauze, and impregnated silver mesh. Patient and his parents were instructed to continue this dressing course BID upon release.

Five days post-hospitalization saw no visible reduction in wound state. Patient expressed distress over necrosis formation at the site and a 5/10 pain level. A trial of Formulation 1 with sterile gauze and paper tape was initiated at this point.

The wound was flushed with sterile saline, blotted dry, and a thin layer of Formulation 1 was applied topically to the wound bed and surrounding tissue. Wound dressing consisted of sterile gauze, kerlix, and paper tape. Patient was instructed to continue dressing changes BID, in the manner described.

By day 3 of treatment with Formulation 1, the wound had visibly improved. The eschar had autolytically debrided and the wound profile showed granular bases with well demarcated borders and the formation of skin islands. Patient reported a reduction of pain to 2/10.

After 10 days of dressing changes utilizing Formulation 1, the epithelial layer of skin had regenerated peripherally with mild central eschars at the central aspect of the wound bases. Pain was eliminated. Patient was able to resume normal activity at 10 days.

A rapid rate of healing, pain reduction, and elimination of necrotic tissue without requiring active debridement was achieved using Formulation 1. This dressing change protocol was significantly more economically effective than advanced impregnated dressings, while providing an appropriate environment for epithelization of the wound bed.

Example 11. The Use of Formulation 1 in the Treatment of Lower Leg Ulceration: Case Report A 70-year-old white man with a history of long-term smoking and DVT progressed to PE. Hospital course involved anticoagulation and IVF placement. Post-hospitalization, he developed bilateral lower leg venous ulcers and a low albumin level was diagnosed. Protein supplement was started along with aggressive dressing changes with honey sheets, unna boot, coban, and ace wrap performed twice a week progressing to weekly. Podiatry followed him twice a month for the acute phase. Albumin level normalized, dressing changes were continued with slow improvement, at which time acceptable healing had resulted and the patient was transitioned to compression stockings.

After one month of not wearing compression stockings, not elevating his extremities, and continuing to smoke, the patient developed a right lower leg ulcer. Given his history of slow healing, a trial of Formulation 1 was initiated. His albumin continued to be normal.

A thin layer of Formulation 1 was applied to and around the ulcer. A honey sheet was then applied followed by an unna boot, coban, and an ace wrap (for compression). This dressing was changed weekly. At each dressing change his leg was cleaned with saline.

After 4 weeks of weekly dressing changes utilizing Formulation 1, the ulcer was significantly smaller versus his prior history of slow healing. He transitioned back to compression stockings much faster.

A significant reduction in healing time was observed by including Formulation 1 versus not using Formulation 1 on this gentleman. His first ulcer was very slow to heal with the honey-only protocol (6-7 months); however, the addition of Formulation 1 with the same dressing technique on a second venous ulceration resulted in a dramatic reduction in healing time.

Example 12. the Use of Formulation 1 in the Treatment of a Pediatric Polymicrobial Infection: Case Report A 9-year-old boy with no significant medical history presented to clinic with an infected lesion to the left lateral chin. His father reports that the boy sustained a mechanical excoriation burn during karate when he fell on a mat. The parents treated the wound topically with bacitracin for 7 days and have noted a worsening of the erythema, edema, and topical warmth to the area with mild purulent drainage. The patient complained of tenderness to palpation. A culture, taken in office, revealed Herpes simplex type 1 and Methicillin Resistant *Staphylococcus aureus* (MRSA).

The patient was treated topically with Formulation 1. The patient's parents were instructed to wash the area gently with water and pat dry. The use of gloves was suggested due to the highly contagious nature of the infecting microorganisms. A thin layer of Formulation 1 was applied twice daily, morning and bedtime, and covered with a Band-Aid. The patient was given strict instructions to refrain from all sports until the infection abated.

The patient's parents reported by day two they the purulent drainage had ceased. The erythema and edema were resolving. By day 3 all edema and erythema had completely resolved. The patient was no longer tender to palpation. By day 7, the infection had completely resolved and the remaining eschar was beginning to loosen from the new epithelium.

The use of Formulation 1 is safe and effective for use on pediatric patient with polymicrobial skin infections. The petrol base is gentle on young skin and treats complicated infections. The ease of use is of particular importance in a pediatric population where swallowing medicines is often a challenge for caregivers. The aggressive treatment of infection in these highly communicable bacterial strains is an attractive feature of this product.

Example 13. the Use of Formulation 1 in the Treatment of Diaper Dermatitis: Case Report Irritant diaper dermatitis is a pervasive form of skin irritation commonly found in infants and toddlers. Prolonged exposure of the skin to irritants exacerbates these attacks. Such irritants include infrequent diaper changes, diarrhea, and contact allergy. The change in topical skin pH causes a breakdown in the epidermis, resulting in a painful erythematous rash to the most prominent areas of the buttocks.

The 4-month old patient was brought to his pediatrician by his parents after an acute onset of irritant diaper dermatitis. The patient exhibited a distressed affect, crying and avoiding pressure to the affect area. Upon physical exam, shiny erythematous raised patches were observed on the convex areas of the buttocks. Skin folds were spared. Parents reported that the rash has been present for 3 days and was worsening. Increased frequency in diaper changes had failed to improve symptoms. The patient had recently been experiencing diarrhea prior to onset which has now subsided.

The patient was assessed and the site of irritation was gently flushed with sterile water. The area was blotted dry and treated with topical application of Formulation 1 to the affected areas and surrounding tissue. A dry diaper was applied and the parents were given instructions for frequent diaper changes with gentle cleaning and application of Formulation 1 at each change.

Upon application the patient was noticeably more comfortable; the crying stopped and the patient began showing interest is a toy, indicating that the pain was subsiding. Twelve hours after the initial treatment the erythema had decreased by 85% and the parents reported that the child had resumed eating, playing, and was no longer fussy. After 18 hours a total resolution of the condition had been achieved.

The stratum corneum, the most superficial layer of skin, is comprised of keratinocytes and is thinner and especially sensitive in young pediatric patients. The third layer, the stratum granulosum, is a lipid producing layer which provides a hydrophobic barrier to the lesser skin layers thus providing a protective barrier to the irritant therefore the irritation is primarily contained to the first two epidermal layers. Formulation 1 has a petrolatum base and is naturally hydrophobic, thereby mimicking the body's natural defense mechanism and speeding healing to the affected area. The antimicrobial properties support the immune system and protect against common infections associated with severe diaper rash.

There are many treatments for irritant diaper dermatitis, the most common of which include zinc based creams, titanium dioxide jellies, anti-fungals, antacids, and corn starch. Research shows that the creams, jellies, and antacids are only minimally effective without application of a petrol layer. Anti-fungals are effective if the cause of the irritation is fungal in nature and often takes a 7-day course to achieve resolution. Lastly, corn starch is thought to prevent chaffing which minimizes discomfort but does not provide rapid relief from symptoms. Formulation 1 is currently the only product which has a petrolatum base that balances the pH of the skin and is capable of treating a polymicrobial infection.

A rapid rate of healing and pain resolution was achieved using Formulation 1. By providing a lipid bilayer, Formulation 1 aids the body's natural defenses to protect skin from pH induced breakdown with a medicated, water proof barrier thus both treating and protecting the skin simultaneously.

Example 14. Treatment of Non-Healing Abrasion with Formulation 1: Case Report

Evidenced based protocols for the treatment of radiodermatitis is scarce and research indications that hospital management of these cases lacks consistency. A literature review in 2010 concluded that there was insufficient evidence to advocate for any one therapeutic option. In addition, a previous study reported an 80-90% incidence of erythematous reactions and a 10-15% incidence of moist desquamation in patients undergoing radiation therapy indicating this condition is a prevalent side effect to radiation therapy. Here, a case of radiodermatitis in which treatment with Formulation 1 was performed is reported.

A 54-year-old female had a history of a soft tissue sarcoma which had been successfully treated with radiation therapy, but consequently suffered an E3 Radiation-Induced Skin Reaction Assessment Scale (RISRAS) type radiodermatitis to the lateral aspect of her right lower extremity.

At 52 years, she experienced increased right distal leg pain and was referred to an oncologist where she was found to have a soft tissue sarcoma. After successful treatment of the sarcoma, which included adjuvant radiotherapy, she presented to the office with a 15.4 cm by 8.8 cm painful, solitary, erythematous plaque to the distal right lateral lower extremity consistent with radiodermatitis.

The occurrence rate of radiodermatitis in patients that underwent radiotherapy has been reported to be as high as 46% in one study. Side effects of this treatment results in increased occurrence of local skin lesions with possible ulceration, pain, and risk of infection.

The patient reported having been previously treated with hyaluronidase-based cream, sucralfate cream, biafine cream, and mepitel but was still experiencing pain and was displeased with the physical aesthetic of the wound. A thin layer of Formulation 1 was applied to and around the affected area. The area was covered with sterile telfa, wrapped with kerlix, and paper tape, taking care to avoid placing adhesive directly in contact with the skin. This dressing was changed twice daily. At each dressing change, the wound was cleaned with sterile saline.

A noticeable reduction in the erythema could be seen after one application and by the end of one week the plaque was almost totally resolved with only mild patchy spotting remaining. Patient reported that her pain had resolved completely and she was pleased with her outcome. In conclusion, Formulation 1 was found to be efficacious in treating radiodermatitis rapidly with no toxicity or side effects. The treatment was also economically efficacious. In future, randomized control trials will be established for further observation of Formulation 1 in treating radiation burns.

Example 15. Treatment of Wagner Grade 2 Ulceration with Formulation 1: Case Report A 72 year old man with cardiovascular disease and well-controlled diabetes mellitis presented to the clinic with an ulcer that had been present for 6 months. The ulcer measured 3.2 cm×1.9 cm×0.2 cm and was staged as a Wagner grade 2. He was married with 3 adult children, did not smoke, drank alcohol socially, and had a family history of various endocrine disorders. He denied previous ulcerations and attributed his ulcer to "a bug bite." Past treatment of his wound had included betadine, silvadene, and hydrogel to the wound bed. At time of presentation, he was applying silvadene every other day with a dry, sterile dressing, but wound measurements indicated poor healing. His medications were metformin, clopidogrel, metroprolol, low dose aspirin, and simvastatin with allergies to ACE inhibitors, penicillin, and sulfa drugs.

The patient presented for assessment of his diabetic ulcers and was found to have an ulcer on the lateral aspect of his calf. The wound base was 40:60 ratio fibrogranular with erythematous borders that extended 6 mm from the wound bed. Surrounding flesh was warm to the touch when compared to the contralateral side. It did not probe to bone, had no tracking, and exudate was moderate. A wound culture grew *Staphylococcus aureus* and pain was reported as 6/10.

Treatment began with mechanical debridement. Wound base was brought to bleeding and a thin layer of Formulation 1 was applied to the ulcer and surrounding tissue. The wound was dressed with a FiltreX bandage and this dressing was left in contact with the wound for 5 days. The patient was permitted to bathe while the FiltreX was in place, as it provides moisture protection. At day five, the home health nurse reported significant granulation and a reduction in the wound size from 3.2 cm×1.9 cm×0.2 cm to 2.1 cm×0.9 cm×0.05 cm.

Ten days into treatment revealed significant epithelialization of the wound bed. The wound measured 1.3 cm×0.4 cm. Depth was no longer measureable as the surrounding tissue had granulated in. The patient reported no further pain, erythema had resolved, and temperature returned to appropriate, indicating a resolution of the inciting infection. Dressing with Formulation 1 and FiltreX was continued for 10 more days at which time the wound was found to be completely resolved with full epithelialization of the wound and the formation of fibrous tissue.

Formulation 1 is an adjunctive therapy for chronic diabetic ulceration. The petrolatum base provides the moisture necessary for proper wound healing without macerating the wound. Furthermore, the non-cytotoxic, anti-microbial properties are conducive to rapid healing in that it allows for unimpeded fibroblastic activity to take place, thereby creating an ideal setting for the body's natural response to wound healing.

With respect to comfort, affordability, and ease of use, Formulation 1 was found to be the ideal treatment formula. The bandage, and subsequently Formulation 1, stays in contact with the wound for up to 7 days. This dressing endurance, both primary and secondary, is unique and minimizes the need for daily interruptions of the patient's life for dressing changes. Additionally, the bandage is hydrophobic which ensures the patient may bathe without concerns of dressing or wound disruption. This is a unique advantage due to the ability to shower making treatment more tolerable. In terms of patient compliance, the comfort and versatility of this dressing combination increases the likelihood that the patient will maintain a proper healing environment thereby leading to more successful outcomes. Ultimately, the combination of Formulation 1 and FiltreX provided the ideal environment for complete resolution of this difficult to heal diabetic ulcer.

Example 16. Treatment of Non-Healing Complicated Skin Tear with Formulation 1: Case Report Skin tears result from a separation of the two major layers of human skin, the epidermis and the dermis. They represent a major problem affecting older adults with prevalence rates between 14% and 24%. An 88 year old white female with a history of Alzheimer's, low albumin, PVD, hypertension, and hypothyroidism had been undergoing unsuccessful treatment for four months in an attempt to manage a complicated skin tear. Many dressing techniques had been attempted with minimal progress, including silver and topical antibiotics. A thin layer of Formula I was applied to and around the wound area. A non-adherent gauze sheet was then applied, followed by an ace wrap (for compression). This dressing was changed weekly. At each dressing change, her leg was cleaned with saline. Within weeks, the wound had stabilized, with complete epithelialization within two weeks. Notable healing can be seen and continues through week eleven. Moreover, while non-adherent regimens were always used, dressing changes were painful to the patient, indicated by visual and auditory responses to the removal of dressing materials from the wound site. While using formulation 1 there was no discomfort/pain response during dressing changes. Formulation 1 added an additional, non-adherent layer of protection, decreasing discomfort while stimulating healing, ultimately resulting in re-epithelialization The use of formulation 1 during the dressing change protocol stimulated healing, protected the site from additional physical insult, and reduced pain during dressing changes. For such non-ambulatory patients, risk of limb loss and infection is very high, and the healing of such a complicated, difficult wound represents a major success.

Example 17. Treatment of Phytophotodermatitis with Formulation I: Case Report

A 38-year-old woman with no significant medical history presented with a 2-day history of an erythematous vesiculobullous plaque with localized edema and erythema. She denied puritis, but admitted to associated burning sensation. Prior to the onset of the lesion, she went hiking near her home during which she picked oranges off of a tree she found. Upon examination, the patient has a central plaque measuring 4.1 cm×3.4 cm with interspersed vesicles/bullae which the patient admitted to draining at home. There are 2 secondary patches: one measuring 0.9 cm and the other 4 mm. The lesions are located on the left anterior shin. They are edematous and erythematous, but without appreciable temperature variation as compared to the contralateral side.

Based on the patient's presentation and recent exposure to citrus plants, she was diagnosed with phytophotodermatitis, a common dermatological condition resulting from contact with furocoumarins under direct sunlight. The result of this exposure causes a phototoxic inflammatory response to the localized area. A common defining feature of this clinical condition is the absence of puritis with the patient complaining of burning instead, which differentiates this from contact dermatitis. There are four species of plants that are known to contain furocoumarins: Apiaceae, Rutaceae, Moraceae, and Leguminosae. Members of Apiaceae include parsnip, celery, and parsley. Rutaceae includes citrus fruits, and is thus the likely culprit in the present case. Figs belong to the Moraceae family and lastly, *Psoralea corylifolia* belongs in Leguminosae family.

The course of this condition begins with the acute phase, which peaks at day 3 and can last 3-5 days. The more concerning aspect of this condition, from the patient standpoint, is the resultant hyperpigmentation which often persists for years. This condition most commonly affects areas that are exposed to the element, such as hands, arms, and lower legs, so patients tend to be distressed over the resultant physical deformity.

A thin layer of Formulation 1 was applied to the plaque and surrounding tissues. The area was covered with sterile telfa, wrapped with kerlix and paper tape, taking care to avoid placing adhesive directly in contact with the skin. This dressing was changed daily. At each dressing change, the wound was cleaned with sterile saline.

After 3 days of application, the acute phase resolved and the post-inflammatory hyperpigmentation set in. The patient continued with daily dressing changes and by 20 days of treatment, the hyperpigmentation was almost totally resolved with only mild patchy spotting remaining.

Formulation 1 was found to be efficacious in treating both the acute and post-inflammatory hyperpigmentation phases of phytophotodermatitis, the latter of which is known to often persist for years. In the future, it is recommended that randomized control trials be conducted with Formulation 1 to treat hyperpigmented lesions.

Example 18. Stability

Formula I as packaged in tubes was subjected to an accelerated stability study. Formula I was placed sideways in a 40° C.±2° C./75%±5% relative humidity (RH) storage chamber for different intervals to yield a period of three months. The product was assessed for physical and analytical characteristics. When stored at 40° C.±2° C./75%±5% (RH) benzyl alkonium chloride was stable as shown in Table 15.

TABLE 15

Accelerated Stability Testing

| Analytical Assay Testing | Specification | Initial: Assessing | 1 Month Assessing | 2 Months Assessing | 3 Months Assessing |
|---|---|---|---|---|---|
| Benzalkonium Chloride 0.0081% | 0.0071%-0.0086% | 0.0084% | 0.0085% | 0.0075% | 0.0086% |

Additionally, the product met specification for appearance, odor, specific gravity, viscosity and package compatibility at all time points tested.

Formula I was also tested under for microbial counts at 40° C.±2° C./75%±5% were as shown below. The results are shown in Table 16.

TABLE 16

Accelerated Stability Testing

| Micro Testing | SPEC | Method | Results Initial Assessing | 1 Month Assessing | 2 Months Assessing | 3 Months Assessing |
|---|---|---|---|---|---|---|
| Total Plate Count (TPC) | <100 cfu/ml | TM-01 | <10 cfu/ml | <10 cfu/ml | <10 cfu/ml | <10 cfu/ml |
| Yeast/Mold | <100 cfu/ml | TM-01 | <10 cfu/ml | <10 cfu/ml | <10 cfu/ml | <10 cfu/ml |
| Enrichment (Pathogens) | Absent | Absent | Absent | Absent | Absent | Absent |
| Pseudomonas | Absent | Absent | Absent | Absent | Absent | Absent |
| S. aureus | Absent | Absent | Absent | Absent | Absent | Absent |
| E. coli | Absent | Absent | Absent | Absent | Absent | Absent |
| Coliforms | Absent | Absent | Absent | Absent | Absent | Absent |
| Salmonella/Shigella | Absent | Absent | Absent | Absent | Absent | Absent |

Additionally, the product met specification for appearance, odor, specific gravity, viscosity and package compatibility at all time-points tested when under standard conditions for over nine months.

Example 19. Effect of Formulation 1 on Bio-Burden in Live Wounds

Fresh wounds on eight patients were treated by applying a thin layer Formulation 1 to the wounds and surrounding tissue. The wounds were dressed with a pressure dressing, and this dressing was left in contact with the wound for one week. The wound was swabbed before treatment and then again at the conclusion of treatment when the dressing was removed after a week. Bio-burden analyses of the swab samples were performed for total microbial count and Staphylococcus count.

TABLE 17

Bio-burden analysis

| | Total Bacteria CFU/Swab | | Staphylococcus spp. CFU/Swab | |
|---|---|---|---|---|
| Sample ID | Pre | Post | Pre | Post |
| Patient 3 | $9.50 \times 10^3$ | $2.10 \times 10^2$ | $1.55 \times 10^4$ | <5.00 |
| Patient 4 | $3.40 \times 10^6$ | $1.87 \times 10^5$ | $2.70 \times 10^6$ | $2.15 \times 10^4$ |
| Patient 5 | $2.97 \times 10^5$ | 5.00 | $5.30 \times 10^2$ | <5.00 |
| Patient 6 | $5.50 \times 10^5$ | N/A | $3.51 \times 10^5$ | N/A |

TABLE 17-continued

Bio-burden analysis

| | Total Bacteria CFU/Swab | | Staphylococcus spp. CFU/Swab | |
|---|---|---|---|---|
| Sample ID | Pre | Post | Pre | Post |
| Patient 7 | $1.06 \times 10^7$ | $4.02 \times 10^5$ | $7.60 \times 10^6$ | $3.00 \times 10^5$ |
| Patient 8 | $6.32 \times 10^5$ | N/A | $2.60 \times 10^4$ | N/A |
| Patient 10 | $7.00 \times 10^6$ | N/A | $2.85 \times 10^4$ | N/A |
| Patient 11 | $3.25 \times 10^6$ | N/A | $1.60 \times 10^6$ | N/A |

The limit of detection for this assay was 5 CFU/Swab. The limit of detection for patient 3 was 10 CFU/Swab. Samples with no microbial recovery are reported as <5.00. Wounds that were completely healed within the seven day period were not swabbed after treatment and were marked N/A.

One week after treatment revealed significant reductions in total microbial counts and staphylococcus counts. This was especially apparent for the staphylococcus counts. In some instances, the wounds were healed within the seven day duration of the experiment, and therefore were not swabbed.

Example 20. Further Examples

Example 1 was repeated with different active ingredients including a 10% aqueous phase of trolamine salicylate for pain reduction, a 4% aqueous phase of lidocaine for pain reduction, a 0.125% aqueous phase of sodium hypochlorite for infection control, and a 4% aqueous phase of chlorhexidine gluconate.

Example 21. Prophetic Examples

The process disclosed in Example 1 will be repeated but with neomycin instead of a cationic biocide. The result will be a stable formulation of neomycin nanodroplets dispersed in petrolatum.

The process disclosed in Example 1 will be repeated but with polymyxin B instead of a cationic biocide. The result will be a stable formulation of polymyxin B nanodroplets dispersed in petrolatum.

The process disclosed in Example 1 will be repeated with mupirocin instead of a cationic biocide. The result will be a stable formulation of mupirocin nanodroplets dispersed in petrolatum.

The process disclosed in Example 1 will be repeated with bacitracin instead of a cationic biocide. The result will be a stable formulation of bacitracin nanodroplets dispersed in petrolatum.

The process disclosed in Example 1 will be repeated with collagen type 1, 2, or 3 in addition to or in the absence of a cationic biocide. The result will be a stable formulation of collage type 1, 2 or 3 nanodroplets dispersed in petrolatum. When used, the cationic biocides may be present as stable nanodroplets.

The process disclosed in Example 1 will be repeated with a soluble anti-inflammatory agent selected from ibuprofen, aspirin, white willow bark, and diclofenac. The result will be a stable formulation of ibuprofen, aspirin, white willow bark, and diclofenac dispersed as nanodroplets in the petrolatum.

What is claimed is:

1. A process for preparing a stable petrolatum-based composition comprising petrolatum and an active ingredient soluble in a polar solvent, the process comprising:
    a) dissolving the active ingredient in a polar solvent to give an active ingredient solution;
    b) heating the petrolatum to a temperature sufficient to cause the petrolatum to melt to give a melted petrolatum and heating the active ingredient solution to a temperature higher than the temperature of the melted petrolatum to give a heated active ingredient solution;
    c) mixing the melted petrolatum and the heated active ingredient solution to give a melted mixture; and
    d) cooling the melted mixture to give the petrolatum-based composition, wherein the petrolatum-based composition comprises greater than 80% by weight petrolatum and contains no emulsifier.

2. The process according to claim 1, wherein the heated active ingredient solution has a temperature that is about 1° C. to about 5° C. higher than the temperature of the melted petrolatum.

3. The process according to claim 1, wherein the active ingredient is a water-soluble active ingredient.

4. The process according to claim 3, wherein the polar solvent comprises water.

5. The process according to claim 1, wherein the active ingredient comprises less than 1% by weight of the petrolatum-based composition.

6. The process according to claim 1, wherein the composition is greater than 90% by weight petrolatum.

7. The process according to claim 1, wherein the polar solvent and active ingredient are dispersed in the petrolatum in the form of nanodroplets.

8. The process according to claim 7, wherein the nanodroplets range in size from about 10 nm to about 10,000 nm.

9. The process according to claim 1, wherein the composition further comprises one or more compounds selected from the group consisting of TGF-alpha, TGF-beta, platelet-derived growth factor (PDGF), epidermal growth factor (EGF), fibroblast growth factor also referred to as keratinocyte growth factor (FGF), vascular endothelial growth factor (VEGF), insulin-like growth factor (IGF), connective tissue growth factor (CTGF), activin, interleukin 1, TNFα, and GM-CSF.

* * * * *